(12) United States Patent
Brown et al.

(10) Patent No.: US 11,183,284 B2
(45) Date of Patent: Nov. 23, 2021

(54) DOSAGE CONFIRMATION APPARATUS

(71) Applicant: Digital Hospital, Inc., San Jose, CA (US)

(72) Inventors: Kevin R Brown, Rescue, CA (US); Philip Curtis, San Jose, CA (US)

(73) Assignee: Digital Hospital, Inc., San Jose, CA (US)

( * ) Notice: Subject to any disclaimer, the term of this patent is extended or adjusted under 35 U.S.C. 154(b) by 336 days.

(21) Appl. No.: 15/829,744

(22) PCT Filed: May 31, 2016

(86) PCT No.: PCT/US2016/035082
§ 371 (c)(1),
(2) Date: Dec. 1, 2017

(87) PCT Pub. No.: WO2016/196504
PCT Pub. Date: Dec. 8, 2016

(65) Prior Publication Data
US 2018/0108435 A1 Apr. 19, 2018

Related U.S. Application Data

(60) Provisional application No. 62/169,484, filed on Jun. 1, 2015.

(51) Int. Cl.
H04N 7/18 (2006.01)
G16H 20/10 (2018.01)
(Continued)

(52) U.S. Cl.
CPC ............ G16H 20/10 (2018.01); A61M 3/005 (2013.01); A61M 31/002 (2013.01);
(Continued)

(58) Field of Classification Search
CPC ..... G16H 20/10; A61M 3/005; A61M 31/002; A61M 3/022; A61M 5/1723;
(Continued)

(56) References Cited

U.S. PATENT DOCUMENTS 3,053,089 A 9/1962 Neyer et al.
3,774,603 A 11/1973 McPhee
(Continued)

FOREIGN PATENT DOCUMENTS

CN 1710389 A 12/2005
CN 101251402 A 8/2008
(Continued)

OTHER PUBLICATIONS

Extended European Search Report dated Jan. 7, 2019 for European Patent Application No. 16804249.7 filed May 31, 2016, pp. 1-8.
(Continued)

Primary Examiner — Jayanti K Patel
Assistant Examiner — Richard B Carter
(74) Attorney, Agent, or Firm — Intellectual Innovations Legal Advisors

(57) ABSTRACT

An apparatus for determining the volume of a liquid in a container. A digital camera is provided to view the container. A processor can optically detect certain characteristics of the container as viewed by the camera and accesses a computer memory having stored characteristics of a plurality of known containers, and the compare the detected certain characteristics with the stored characteristics to identify the container from the plurality of known containers. The processor can calculate the volume of the container as a function of the distance between the first and second ends of the container as viewed by the camera. The processor can receive at least one image from the camera and determine whether the liquid in the container contains any air pockets
(Continued)

based on the at least one image. Methods are provided, including a method for use by an apparatus having a camera and a processor electrically coupled to the camera to confirm the dosage of a medicament in a container.

24 Claims, 23 Drawing Sheets

(51) Int. Cl.
| | |
|---|---|
| G01F 22/00 | (2006.01) |
| G06K 9/00 | (2006.01) |
| G01F 23/292 | (2006.01) |
| A61M 3/00 | (2006.01) |
| A61M 31/00 | (2006.01) |
| A61M 3/02 | (2006.01) |
| A61M 5/172 | (2006.01) |
| G01F 22/02 | (2006.01) |

(52) U.S. Cl.
CPC .......... *G01F 22/00* (2013.01); *G01F 23/2921* (2013.01); *G06K 9/00* (2013.01); *A61M 3/022* (2014.02); *A61M 5/1723* (2013.01); *A61M 2205/50* (2013.01); *G01F 22/02* (2013.01); *G06K 2209/01* (2013.01); *Y02A 90/10* (2018.01)

(58) Field of Classification Search
CPC ................ A61M 2205/50; G01F 22/00; G01F 23/2921; G01F 22/02; G06K 9/00; G06K 2209/01; Y02A 90/26
USPC .............. 348/127; 705/2; 141/153; 206/534; 382/100; 250/223 B; 356/440; 73/293
See application file for complete search history.

(56) References Cited

U.S. PATENT DOCUMENTS

| | | | |
|---|---|---|---|
| 4,107,993 A | 8/1978 | Shuff et al. | |
| 4,633,711 A * | 1/1987 | Hippie ................ | G01F 23/2922 73/293 |
| 4,733,095 A | 3/1988 | Kurahashi et al. | |
| H1045 H | 5/1992 | Wilson | |
| 5,394,732 A | 3/1995 | Johnson et al. | |
| 5,427,161 A | 6/1995 | Luehmann et al. | |
| 5,539,386 A | 7/1996 | Elliott | |
| 6,098,029 A * | 8/2000 | Takagi ...................... | G06T 7/60 382/100 |
| 6,782,122 B1 * | 8/2004 | Kline .................... | G01F 23/292 250/223 B |
| 7,499,581 B2 | 3/2009 | Tribble et al. | |
| 7,982,201 B2 | 7/2011 | Bryant et al. | |
| 8,141,417 B2 | 3/2012 | Gibson et al. | |
| 8,161,810 B2 | 4/2012 | Cadieux et al. | |
| 8,208,144 B2 | 6/2012 | Palumbo | |
| 8,381,581 B2 | 2/2013 | Walsh et al. | |
| 8,539,812 B2 | 9/2013 | Stringham et al. | |
| 8,570,496 B2 | 10/2013 | Chen | |
| 8,817,258 B2 | 8/2014 | Whalley et al. | |
| 2002/0154809 A1 * | 10/2002 | Yamagishi ........... | G01N 21/909 382/142 |
| 2003/0121322 A1 | 7/2003 | Spillman et al. | |
| 2006/0249423 A1 * | 11/2006 | Reijonen ................. | G06K 9/00 206/534 |
| 2007/0107801 A1 * | 5/2007 | Cochran ............... | G01F 13/006 141/153 |
| 2009/0107234 A1 | 4/2009 | Kim et al. | |
| 2009/0223290 A1 * | 9/2009 | Dietz .................. | G01F 23/2924 73/293 |
| 2009/0235737 A1 | 9/2009 | Lavon et al. | |
| 2009/0299279 A1 | 12/2009 | Richter et al. | |
| 2010/0218600 A1 | 9/2010 | Auge et al. | |
| 2011/0178359 A1 | 7/2011 | Hirschman et al. | |
| 2013/0293706 A1 | 11/2013 | Pison et al. | |
| 2014/0247295 A1 * | 9/2014 | Hussain ............... | G09G 3/3406 345/691 |
| 2014/0247296 A1 * | 9/2014 | Nose .................... | B41J 2/17566 347/6 |
| 2014/0300727 A1 | 10/2014 | Matthias et al. | |
| 2014/0320632 A1 | 10/2014 | Matthias et al. | |
| 2015/0178674 A1 * | 6/2015 | Yonaha .................... | G06K 9/20 705/2 |
| 2017/0105558 A1 * | 4/2017 | Andreas ............. | A47G 19/2261 |

FOREIGN PATENT DOCUMENTS

| | | | | |
|---|---|---|---|---|
| CN | 101526384 A | | 9/2009 | |
| CN | 101937632 A | | 1/2011 | |
| CN | 101995281 A | | 3/2011 | |
| CN | 102147281 A | | 8/2011 | |
| CN | 102095469 B | | 8/2012 | |
| CN | 102768054 A | | 11/2012 | |
| DE | 19605006 C1 | | 8/1997 | |
| DE | 19800131 C1 | | 5/1999 | |
| DE | 10151681 A1 | | 5/2003 | |
| DE | 202007012086 U1 | | 12/2007 | |
| DE | 102008007970 A1 | | 8/2009 | |
| DE | 102011055455 A1 | | 5/2013 | |
| DE | 202015101687 U1 * | | 7/2016 | ............. G01K 13/02 |
| EP | 0174178 A1 | | 3/1986 | |
| GB | 1285876 A | | 8/1972 | |
| GB | 1359161 A | | 7/1974 | |
| GB | 2473310 B | | 10/2013 | |
| KR | 20130041716 A | | 4/2013 | |
| WO | WO-03097516 A1 * | | 11/2003 | ............. B67C 3/208 |

OTHER PUBLICATIONS

Response dated Aug. 5, 2019 for Extended European Search Report dated Jan. 7, 2019 for European Patent Application No. 16804249.7 filed May 31, 2016, pp. 1-10.
Getting started with Insulin Injections, Becton Dickinson Canada Inc, Retrieved from Internet: URL: https://www.bd.com/resource.aspx?IDX=3260, 2005, 24 pages.
International Preliminary Report on Patentability for Application No. PCT/US2016/035082, dated Aug. 16, 2017, pp. 1-15.
International Search Report for Application No. PCT/US2016/035082, dated Oct. 17, 2016, pp. 1-4.
Saravanan M., et al., "Non-Contact, Opaque Type Liquid Level Indicator," International Journal of Emerging Technology and Advanced Engineering, Apr. 2003, vol. 3 (4), pp. 638-640.
Wang T., et al., "Liquid-level Measurement Using a Single Digital Camera," Measurement, Oct. 2008, vol. 42, pp. 604-610.
Written Opinion for Application No. PCT/US2016/035082, dated Oct. 17, 2016, pp. 1-6.
Yu C., "Liquid Level Measurement by Using an Image Method," Signal Processing (ICSP), 2014 12th International Conference on, Oct. 19-23, 2014, IEEE, pp. 2320-2323.

* cited by examiner

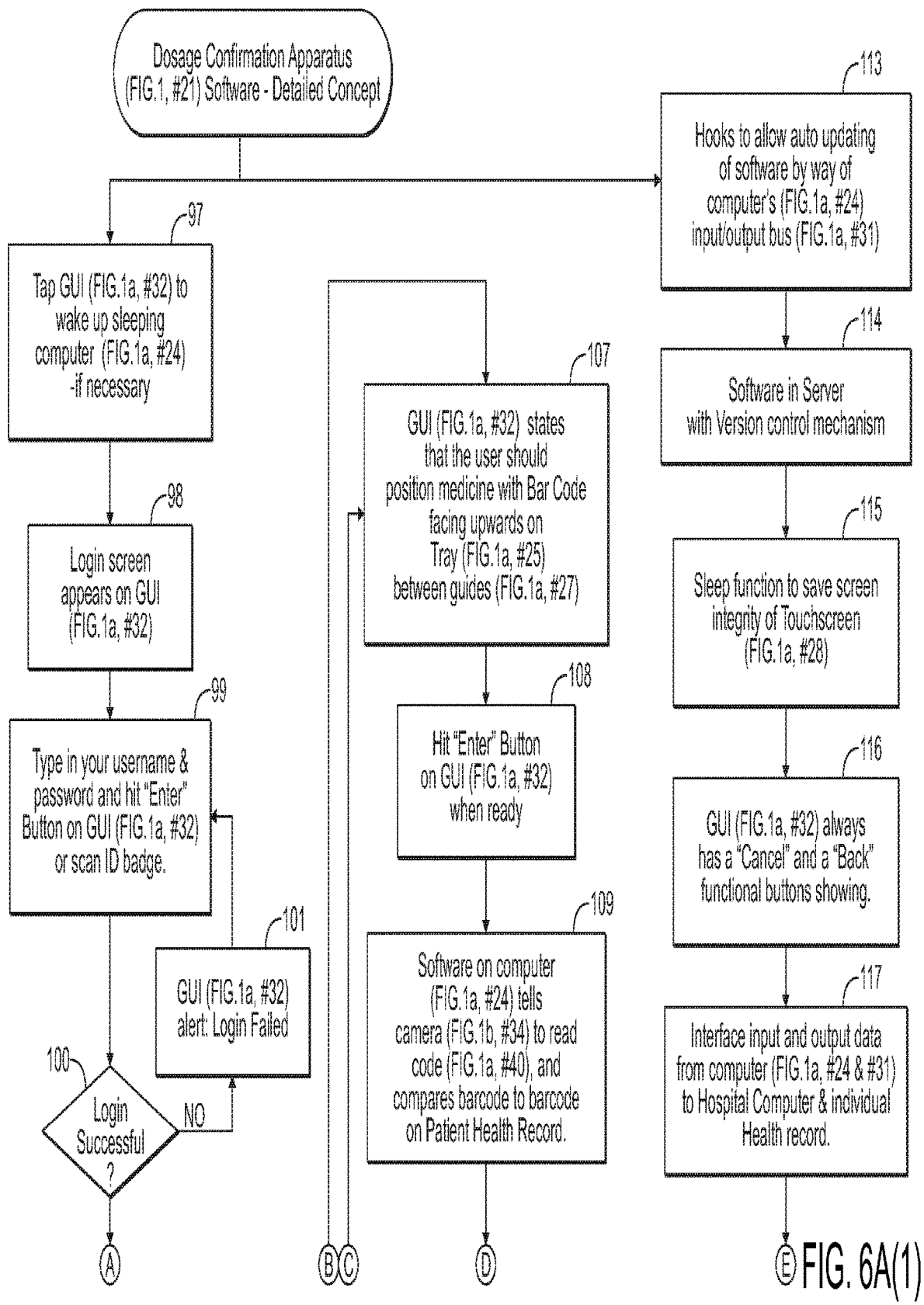
FIG. 6A(1)

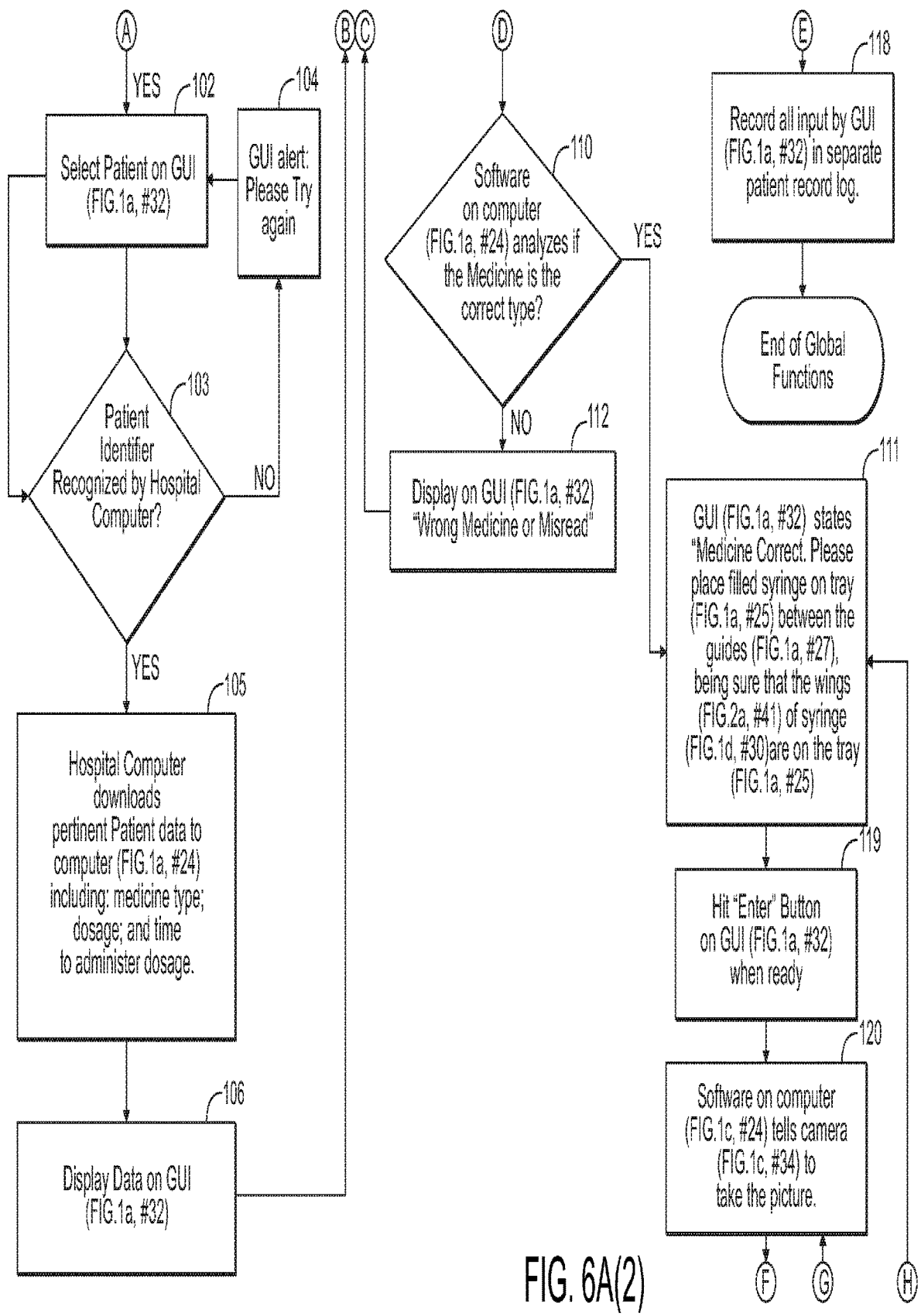
FIG. 6A(2)

_US 11,183,284 B2_

DOSAGE CONFIRMATION APPARATUS

CROSS REFERENCE TO RELATED APPLICATION

This application claims priority to International Application Number PCT/US2016/035082 filed May 31, 2016, which claims the benefit of U.S. provisional application Ser. No. 62/169,484 filed Jun. 1, 2015, the entire content of each of which is incorporated herein by this reference.

FIELD OF THE INVENTION

The present invention relates to the measurement of liquids in containers, and more particularly to the measurement of liquid in containers using digital containers.

BACKGROUND

Human practices, including the practices of medicine, manufacturing, and science can include adverse events. Medical adverse events can result in undesired harmful effects on patients. Reducing such medical adverse events would be desirable.

Apparatus and equipment have been provided for determining the characteristics of liquid in containers, for example in syringes. Improvements in the ease and use of such apparatus and equipment would be desirable.

BRIEF DESCRIPTION OF THE DRAWINGS

The drawings described herein are for illustration purposes only and are not intended to limit the scope of the present disclosure in any way. In the drawings, closely related figures have the same number but different alphabetic suffixes.

FIG. 3b shows a close-up view of the light refractions of the clear liquid filled syringe area of the light ray diagram of FIG. 3a.

FIG. 6a-6c show one embodiment of a flow diagram delineating the operation of the software of the apparatus of FIG. 1.

DETAILED DESCRIPTION

Figure 1:
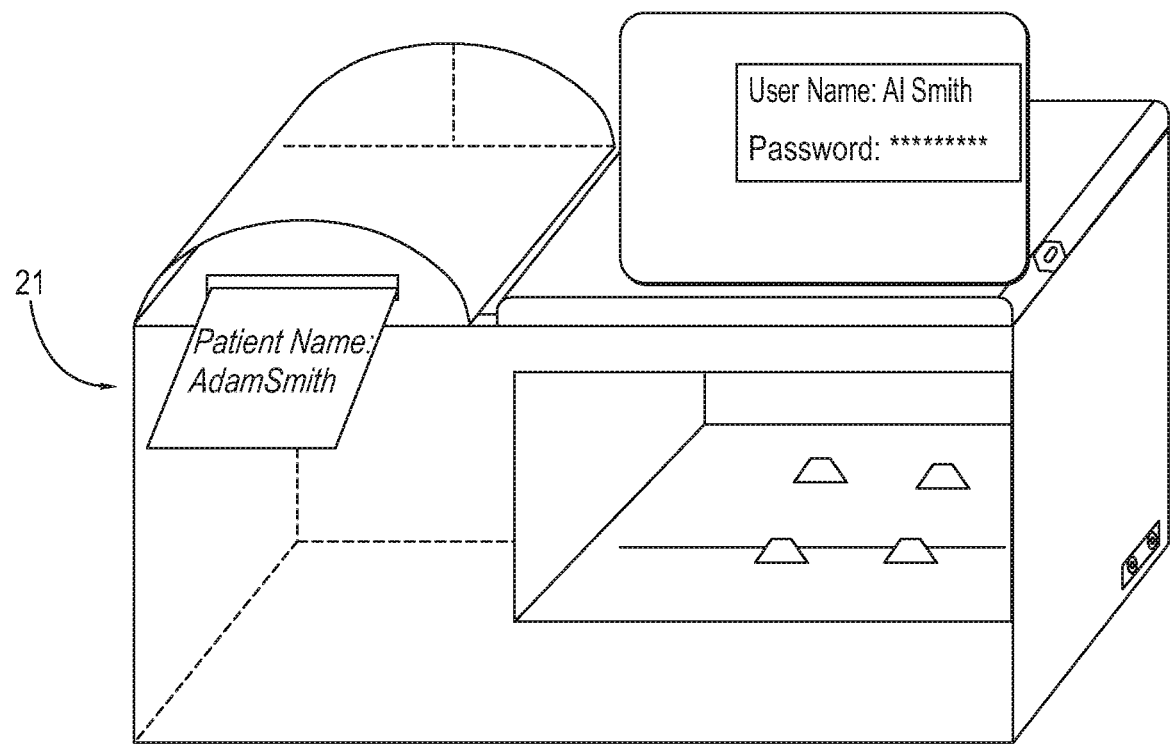
FIG. 1 shows an embodiment of the apparatus of the invention, as the apparatus might appear to medical personnel.

The invention's computer vision awareness of the presence and volume of liquid and air by watching the refraction behavior of light through clear liquid and air could be applied to possibly help lessen adverse events in medicine, manufacturing, and science.

One embodiment of the apparatus of the invention can lessen medical adverse events in the preparation process for injecting medicines into patients in the hospital. Some of the ways in which said medical adverse events can occur are from an incorrect medicine being injected; or from an incorrect dosage of medicine being injected; or from air being present in an injected dose. In some current standard hospital procedures for medical injections, one medical practitioner prepares the dose in a syringe while a second medical practitioner is required for the purpose of checking said preparation process. In one embodiment, the apparatus of the invention can replace the need for said second medical practitioner by supplying the expertise to check said preparation process. The apparatus of the invention can also add the value of recording every step of each iteration of said preparation.

In the case of insulin, a diabetic patient can need at least three and maybe four injections of insulin per day while in the hospital. Effective dosage of said injections is dependent on the most current known blood glucose level of said patient. In one embodiment, the apparatus of the invention can automatically retrieve the most recent known blood glucose level of said patient from said patient's Electronic Health Record (EHR). Effective after release treatment of said patient requires the knowledge of past dosages and the effect said past dosages had on the blood glucose level of the patient. The apparatus of the invention can have access to that data in the EHR.

In one embodiment, an apparatus is provided for determining the volume of a liquid in one of a plurality of known containers. The apparatus includes a digital camera for viewing the container. A processor can be electrically coupled to the camera and configured to optically detect certain characteristics of the container viewed by the camera and to access a computer memory having stored characteristics of the plurality of known containers. The processor can be configured to compare the detected certain characteristics with the stored characteristics to identify the container from the plurality of known containers. The processor can be configured to calculate the volume of the container as a function of the distance between the first and second ends of the container as viewed by the camera.

In one embodiment, an apparatus is provided for determining the presence of any air pockets in a volume of a liquid in a container. The apparatus includes a digital camera for viewing the liquid within the container and providing at least one image of the liquid within the container. A processor is electrically coupled to the camera for receiving the at least one image from the camera. The processor can be configured to determine whether the liquid contains any air pockets based on the at least one image.

In one embodiment, a method is provided to confirm the dosage of a medicament in a container. The method can utilize an apparatus having a camera and a processor electrically coupled to the camera. In the method, the proper volume of the dosage is accessed from a computer memory. The container is viewed with the camera to obtain at least one image of the container. The at least one image of the container is delivered to the processor. The processor calculates the volume of the liquid in the container utilizing the at least one image and compares the calculated volume to the proper volume.

The embodiments of the invention set forth below are examples of the invention, and may in some instances be broader than the foregoing embodiments of the invention but are not intended to limit the breadth of the foregoing embodiments. Additional features of the invention set forth in such embodiments are optional. A feature of any embodiment set forth below can be combined with any of the foregoing embodiments, with or without any other feature of any embodiment set forth below. All characteristics, steps, parameters and features of the apparatus and methods below are not limited to the specific embodiments or specific parts set forth below, but instead are equally applicable to any or all of the foregoing embodiments of the invention and to all embodiments of the invention. Broad terms and descriptors are replaced herein with more specific terms and descriptors not to limit a disclosure to a specific term or descriptor but merely for ease of discussion and understanding.

The apparatus and method of the invention can be used with any suitable container for holding a liquid. One suitable container is syringe (30). One suitable syringe includes a barrel (201) or cylinder for containing a liquid and having a first end (202) provided with a fluid exit port (not shown) and a second end (203) provided with an opening (206) (see FIG. 1d). The syringe can additionally include a suitable plunger, such as plunger (42) having an end (207) for extending through the opening (206) in the barrel (201) for slidable disposition in the barrel.

Figure 1A:
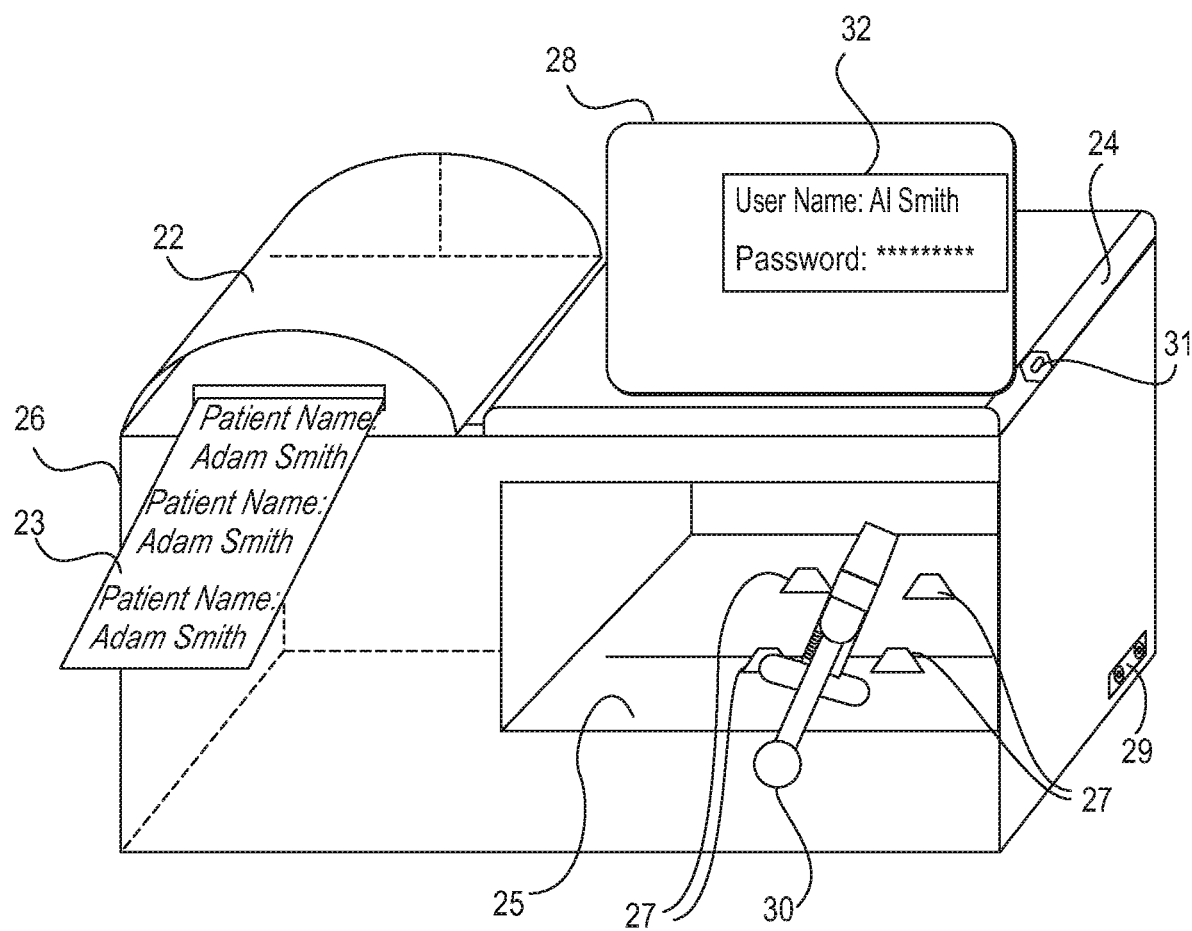
FIG. 1a shows the apparatus of FIG. 1 with a syringe or container having first and second ends placed on the transparent tray.

The apparatus of the invention can be of any suitable type and is not limited to the disclosure and drawings herein. One embodiment of the apparatus of the invention is illustrated in FIGS. 1 and 1a. In FIG. 1a, labeled parts on the exterior of apparatus (21) include touchscreen (28), which can serve as a display and as an input device, graphical user interface software or GUI (32) displayed on the touchscreen (28) and a computer (24) or other suitable processor of any suitable type. In one embodiment, the computer includes a central processing unit (CPU) and memory coupled to the CPU. The memory can include any suitable storage memory, for example hard drives and/or solid state drives, as well as short term member such as random access memory. The computer can be programed in any suitable memory, including by means of software or firmware. Any such software can be stored in the memory of the computer 24, or in the memory of a remote computing device in communication with the computer 24. FIG. 1a also labels the exterior housing (26) or structure of the apparatus (21), the printer (22) which can printout the attachable label (23) with all pertinent data and scan codes. Said label (23) can be attached by medical personnel to the syringe (30) or container having first and second ends. FIG. 1a labels the power supply (29), and also the data connection port (31) to be used for receiving and transmitting data. FIG. 1a labels the transparent tray (25) on which the medicine vial or syringe (30) or other suitable container having first and second (202,203) ends can be placed in order for the computer (24) to process said medicine vial or syringe (30) or container having first and second ends. FIG. 1a also labels the guides (27) on top of the tray (25). Said guides can be used so the medical practitioner visually knows where the syringe (30) or container having first and second ends is to be placed horizontally. In one embodiment of the apparatus of the invention, the syringe (30) or container having first and second ends on the tray (25) such that cap (43) or first end (202) is inserted first into the apparatus (21) and onto the tray 25. In one embodiment, the syringe (30) or container having first and second ends is placed on the tray 25 so that both the cap (43) or first end and the wings or flanges (FIG.

2*a*, #41) of the syringe (30) or container having first and second ends are contained by the front and back boundaries of the tray (25).

Standard hospital insulin preparation process, which is to be checked and recorded by the apparatus (21), starts with examining whether the correct medicine is being used.

Figure 1B:
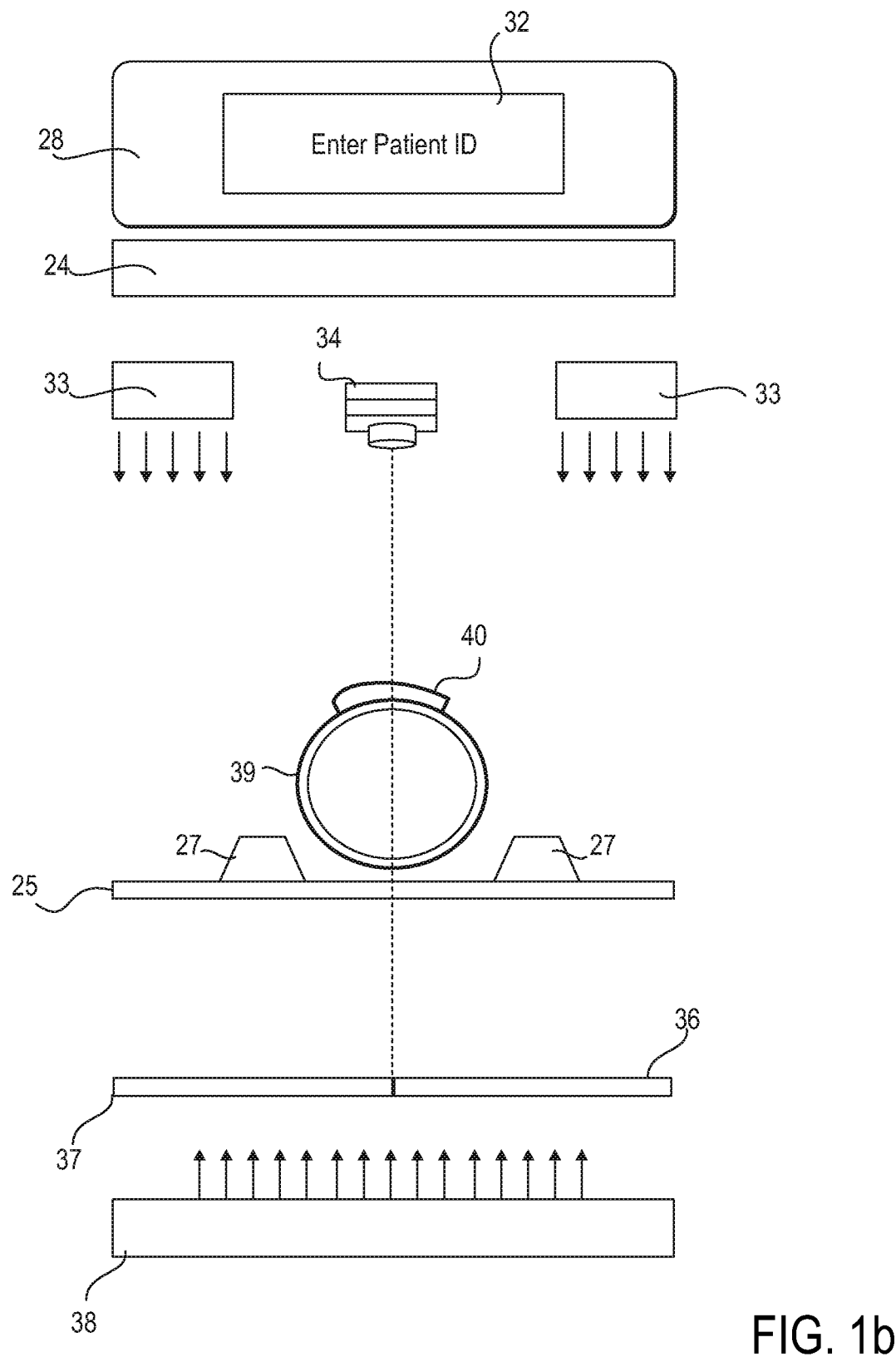
FIG. 1b shows an exploded schematic head-on view of the apparatus of FIG. 1 looking from the front of the apparatus showing one embodiment of elements for analyzing a vial's label including analyzing barcodes on the label.

FIG. 1*b* shows one embodiment of a frontal head-on two dimensional cross section schematic top-to-bottom view of the positioning of the elements of the apparatus (21) that may come into play in order to analyze whether the correct medicine is present. In one embodiment, the analysis of apparatus (21) is commenced by having the medical practitioner place the vial of medicine (39) on the transparent tray (25) between the guides (27) under the camera (34) with the barcode facing upward towards the camera. Standard barcode reading techniques can then be used by the computer (24) while receiving the image from the camera (34). The apparatus (21) can alert medical personnel quickly and easily, for example thru GUI (32), if an incorrect medicine is present before the medicine is administered to the patient.

FIG. 1*b* also shows a frontal head-on two dimensional cross section schematic top-to-bottom view of one embodiment of the positioning of the elements of the apparatus (21) that may come into play in order to analyze whether the medicine is current or expired. In one embodiment, the analysis of apparatus (21) is commenced by having the medical practitioner place the vial of medicine (39) on the transparent tray (25) between the guides (27) under the camera (34) with the barcode facing upward towards the camera. Standard barcode reading techniques can then be used by the computer (24) while receiving the image from the camera (34). If the barcode does not yield the expiration date information, the computer (24) can use standard character recognition of printing on the label (40) to decipher the expiration date. If standard character recognition does not yield satisfactory results, the medical practitioner can be asked, for example by the GUI (32), to enter the expiration date that is on the label using the touchscreen (28) or any other suitable input technique and device. The apparatus (21) can thus alert medical personnel quickly and easily if an expired medicine is present before being administered to the patient.

Figure 1C:
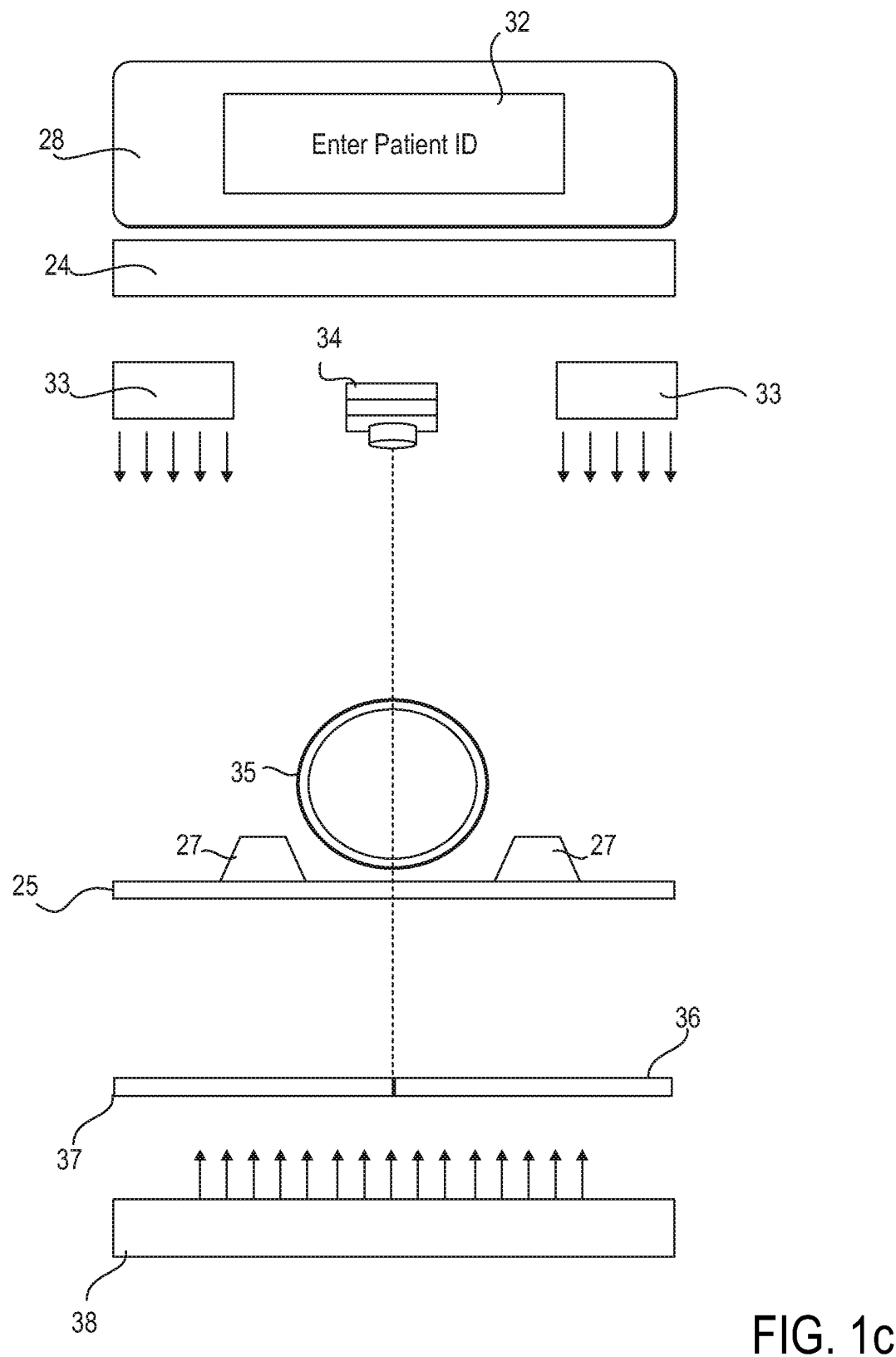
FIG. 1c shows a schematic of a direct head-on view similar to FIG. 1b from the front of the apparatus showing one embodiment of elements used for analyzing a syringe or container having first and second ends.

FIG. 1*c* shows a frontal head-on two dimensional cross section schematic top-to-bottom view of one embodiment of the positioning of the elements of the apparatus (21) that can come into play in order to analyze whether the cap or first end is on the syringe (30) or container having first and second ends, and whether the correct syringe (30) or container having first and second ends is present, and whether the dosage in the syringe (30) or container having first and second ends is correct. In one embodiment, the analysis of apparatus (21) is commenced by having the medical practitioner place the syringe (30) or container having first and second ends on the transparent tray (25) between the guides (27). In one embodiment of the apparatus of the invention, the syringe (30) or container having first and second ends can be placed on the tray (25) such that cap (FIG. 1*d*, #43) or first end is inserted first into the apparatus (21) and onto the tray 25. In one embodiment, the syringe (30) or container having first and second ends is placed on the tray 25 so that both the cap (FIG. 1*d*, #43) or first end and the wings or flanges (FIG. 2*a*, #41) of the syringe (30) are contained by the front and back boundaries of the tray (25). Such placement allows the camera to see said wings or flanges (FIG. 2*a*, #41) and said cap (FIG. 1*d*, #43) or first end to later decipher the size of the syringe or container having first and second ends.

In one embodiment, the camera (34) can take a picture using top lighting (33). Standard computer vision software in the computer (24) can use object identification to decide whether the cap (FIG. 1*d*, #43), or first end, is present or is not present on top of the syringe (30) or container having first and second ends. In one embodiment, the cap or first end is required to be on. Analysis procedures of the apparatus (21) concerning whether the correct syringe (30) or container having first and second ends (202,203) is present, and whether the dosage in the syringe (30) or container having first and second ends is correct, is discussed later in this text with respect to the FIG. 2 series and the FIG. 3 series of drawings. For now, please note that in one embodiment the line where the Color Number One Transparency (36) or filter meets the Color Number Two Transparency (37) or filter is ideally aligned with the center of the syringe (30) or container having first and second ends and the center of the lens of the camera. This is one preferred placement situation, although it is appreciated that the syringe or container having first and second ends may be placed off center in the operation of the apparatus (21), as will be discussed later when referring to FIGS. 2*b* and 2*c*.

Figure 1D:
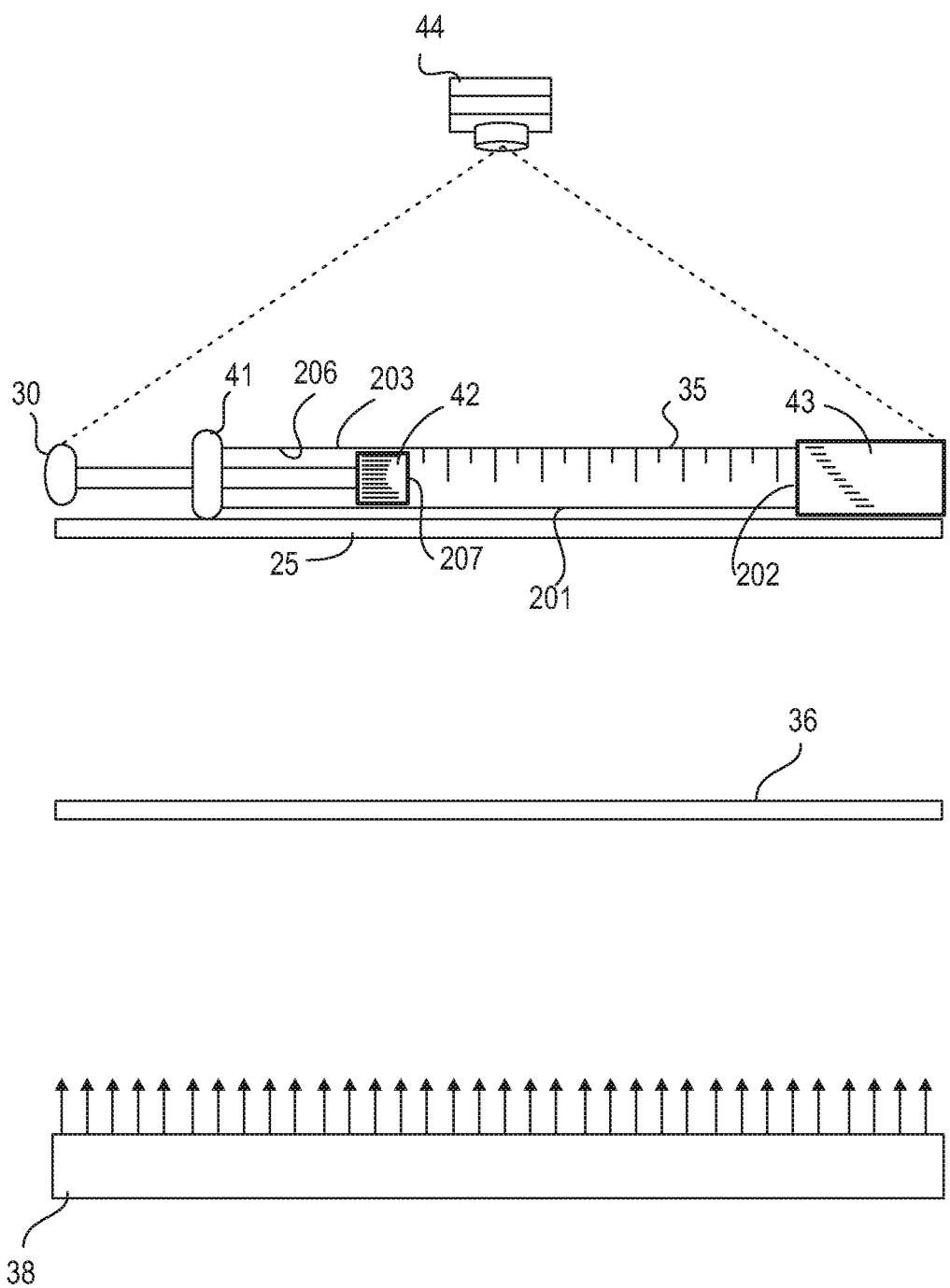
FIG. 1d shows a side view schematic of the apparatus of FIG. 1 with the viewer looking on from the right side of apparatus. The schematic shows the side view of camera (44) looking from the right side, the syringe (30), the transparent tray (25), the color number one transparency (one of two) (36) or filter looking on from the right side of apparatus (21), and the bottom light source (38) of the light assembly of the apparatus (21) of the invention of FIG. 1.

FIG. 1*d* shows one embodiment of a side view, two dimensional cross section schematic of the positioning of elements of the apparatus (21) and the syringe (30) or container having first and second ends. FIG. 1*d* is looking directly towards the right side of the apparatus (21) so that the rear of the apparatus (21) is to the right of the image and the front of the apparatus (21) is to the left of said image. FIG. 1*d* shows that the Color Number One Transparency (36) or filter, and by implication also the Color Number Two Transparency (37) or filter which is blocked from view, are in one embodiment at least as long as the longest syringe (30) or container having first and second ends being testing on the apparatus (21). In one embodiment, the depth of the tray (25) can be at least as long as the longest syringe (30) or container having first and second ends testing on the apparatus (21). Compare FIG. 1*d* with both FIGS. 1*a* and 1*c* to get two perspectives on the positioning of syringe (30) or container having first and second ends and the positioning as well as size of Color Number One Transparency or filter (36) and Color Number Two Transparency (37) or filter and tray (25).

Figure 2A:
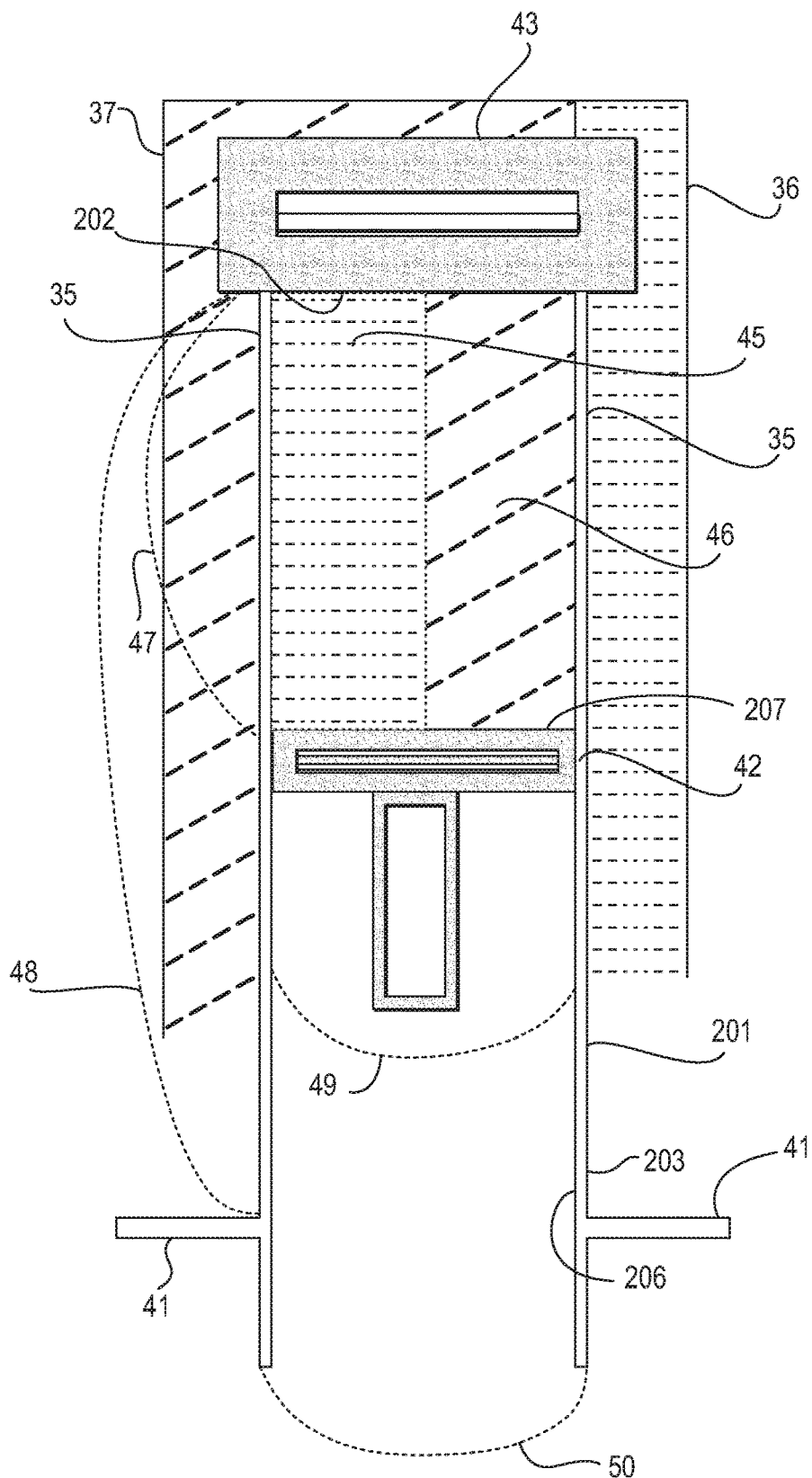
FIG. 2a shows one embodiment of the view of the camera of the apparatus of FIG. 1 looking downwards onto the syringe or container having first and second ends full of clear liquid.

FIG. 2*a* portrays one embodiment of the view the camera (34) of the following: a clear liquid filled syringe (30) or container having first and second ends, the Color Number One Transparency (36) or filter, and Color Number Two Transparency (37) or filter. The bottom lighting (38) is in effect but the camera does not see the actual bottom lighting apparatus (38) which is below the transparencies or filters.

In one embodiment, the apparatus (21) can determine whether the syringe (30), or container having first and second ends, is the correct size of syringe, or container having first and second ends, for the desired dose. In one embodiment, the process of the computer (24) which decides on the correctness of the size of the syringe, or container having first and second ends, determines the length of the cylinder (48). The length of the cylinder (48) can be defined as the distance from where the bottom of the cap (43) or first end meets the wall of syringe cylinder (35) to where the wings or flanges (41) meet the cylinder wall (35). Standard computer vision programming of computer (24) can use object recognition to determine exactly where said two points are, and then computer (24) can calculate the length of the cylinder (48). Once the length of the cylinder (48) has been calculated, computer (24) can compare said calculated length with known cylinder lengths of different size syringes, or containers having first and second ends, and decide if the desired syringe, or container having first and second ends, is in place and report to medical personnel through GUI (32) or otherwise. In one embodiment, the computer can store in memory the length of the cylinder of a finite number of syringes, or containers having first and second ends. Most of the said syringe cylinder length data in memory has the property of one unique length per type of syringe, in which case syringe type can be ascertained by calculating the length of the syringe cylinder and associating that length in the stored library of data with a stored type of syringe. It is appreciated that differing syringe or container having first and second ends types may have the same cylinder length and such types should be noted in the computer's stored data and should contain additional differentiating data such as cylinder width (50) (see FIG. 4b). Such length, or other characteristics of the cylinder or other parts of a finite number of syringes, can be stored in any suitable location, such as in memory in any suitable location. Such memory, or storage, can be included in the apparatus or located remote or offsite from the apparatus.

In one embodiment, the apparatus (21) determines whether there is only liquid in the syringe (30) or container having first and second ends, or conversely, whether there is air in the syringe or container having first and second ends. FIG. 2a portrays a syringe (30), or container having first and second ends, filled with liquid. Computer (24) can notice the transposing positions of color when liquid is in the cylinder. In one embodiment, the color one of two (45), or first color, is on the left of the cylinder while the transparency creating that color (36) is on the right of the cylinder. Accordingly, the color two of two (46), or second color, is on the right of the cylinder while the transparency or filter creating that color (37) is on the left of the cylinder.

In one embodiment, two distinct colors for the transparencies (36,37) are utilized, such that the color hue value of each color can be used in addition to saturation and intensity values to distinguish the two colors. Use of color hue values can be an improvement over using strictly light intensity in the computer vision analysis algorithms, as for example would be the case if black and white were used. Use of color hue values can improve the ability of the algorithm to distinguish between the two colors in varying ambient light conditions, both improving accuracy and repeatability of the measurements.

The physics of transposition of colors through a liquid are explained below in the discussion of the FIG. 3 series of illustrations. The apparatus (21) can tell that the cylinder in FIG. 2a is filled with liquid by computer (24) discerning the existence of the transposed colors which appear in an orderly transposition throughout the cylinder.

Once the apparatus (21) has decided that there exists a cylinder full of liquid, the apparatus (21) can measure the volume of liquid inside the cylinder in order to decide if the correct dosage is present. Looking at what FIG. 2a portrays, computer (24) can discern the length of the liquid (47), defined as the distance from where the bottom of the cap (43) or by the first end (202) of the barrel (201) extending between the wall of syringe cylinder (35), to where the top of the plunger (42) or second end (207) extends between the cylinder wall (35). Standard computer vision software in computer (24) can use object recognition to determine exactly where said two points are, and then computer (24) can calculate the length of the liquid (47) between such two ends (202) and (207). To measure the width of the liquid, computer (24) can be programmed with the width of liquid in known syringe sizes, or known container having first and second ends sizes. Alternatively, computer (24) can count the pixels of color from the inside edge of the left cylinder wall (35) to the inside edge of the right cylinder wall (35). Computer (24) can translate the number of pixels into distance and thereby discerning the width of the liquid (49). Once the length and width of the liquid is known, volume can be calculated by the formula $$L * \pi r^2$$

where L=length of liquid in cylinder (48) and r=0.5*width of liquid in cylinder (49).

The computer (24) can then check to see if said volume coincides with the desired volume of medicine. If the volume coincides with the desired volume of medicine, the medical personnel is alerted through GUI (32) or otherwise and the process is allowed to continue. Apparatus (21) can alert medical personnel thru GUI (32) or otherwise if an incorrect dosage of medicine is present and suggestions can be made through GUI (32) or otherwise to correct the situation (see for example the bottom of FIG. 5 for "Correct Volume" decision.)

Figure 2B:
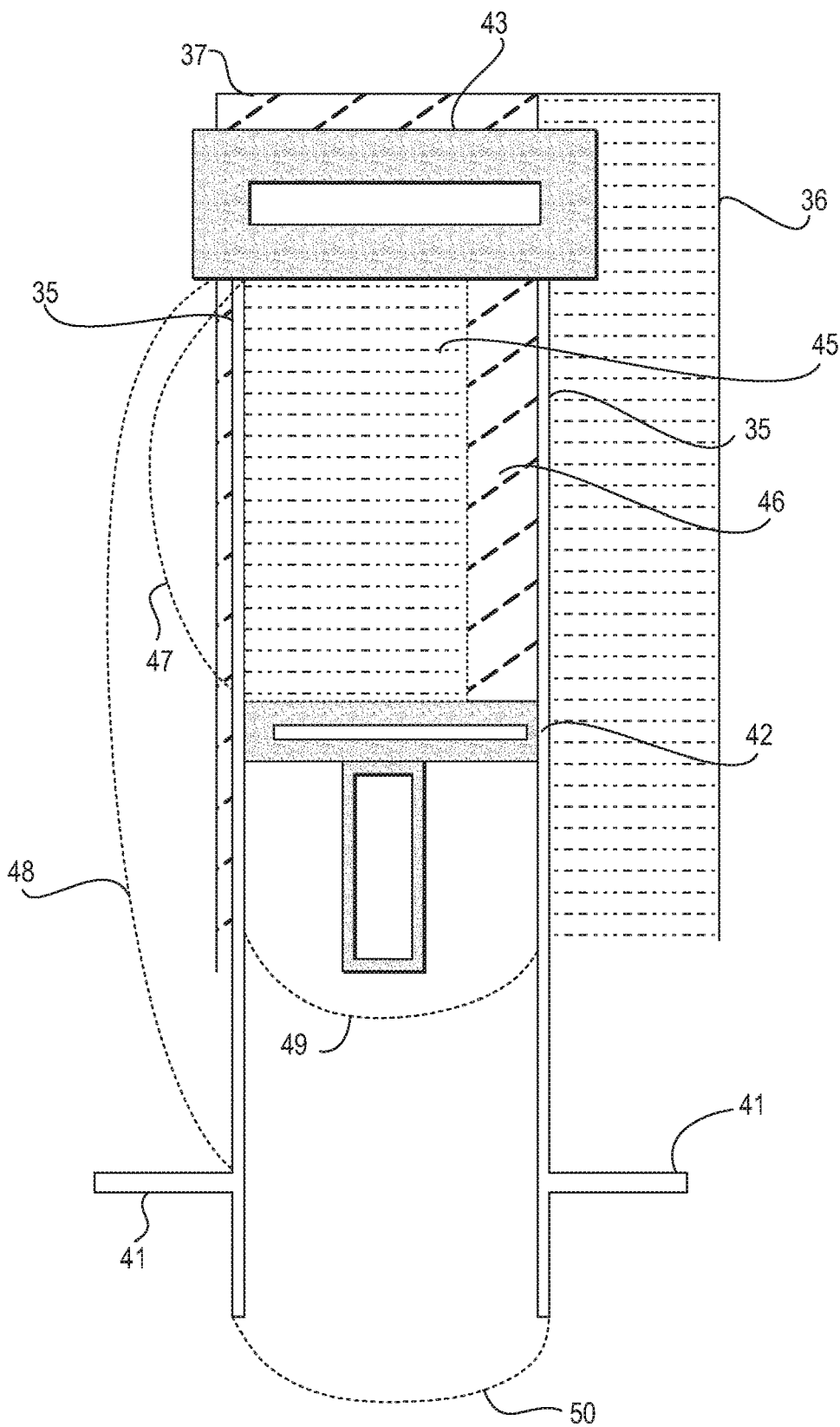
FIG. 2b shows one embodiment of the view of the camera of the apparatus of FIG. 1 looking downwards onto the syringe or container having first and second ends full of clear liquid as the syringe or container having first and second ends is placed off center to the left.

In one embodiment, the apparatus (21) can allow for a certain amount of horizontal leeway when placing the syringe (30), or container having first and second ends, on the top of tray (25) in between the guides (27). FIG. 2b shows one embodiment of the view of the camera (34) looking downwards onto the syringe (30) or container having first and second ends full of clear liquid as the syringe (30) or container having first and second ends is placed to the left, off center of the line between the two transparencies or filters. Color one of two (45) or first color is on the left of the cylinder while the transparency or filter creating that color (36) is on the right of the cylinder. FIG. 2b shows the transposing positions of color when liquid is in the cylinder, but with differing amounts of each color. Accordingly, the color two of two (46) is on the right of the cylinder while the transparency creating that color (37) is on the left of the cylinder. The process of transposition of colors through a liquid will be explained below in the discussion of the FIG. 3 series of illustrations. The apparatus (21) can determine that the cylinder in FIG. 2b is filled with liquid by computer (24) discerning the existence of the transposed colors which appear in an orderly transposition throughout the cylinder, even if the syringe or container having first and second ends is off center. In one embodiment, the existence of both of the two transposed colors prove liquid is in the cylinder, no matter what the ratio of color one (45) or first color is to color two (46) or second color. Thus there is a certain amount of play in the left or right positioning of the syringe or container having first and second ends, which makes it easier for the medical personnel to use the apparatus (21). The ratio of colors produced by a syringe (30) or container having first and second ends placed off the center line of the two transparencies to the right instead of the left would similarly still be able to be analyzed by the apparatus (21). The play in the left and right positioning of the syringe (30) or container having first and second ends is increased as the syringe (30) or container having first and second ends is moved a greater distance above the focal point (73) seen in FIG. 3a and FIG. 3b.

In one embodiment, the apparatus (21) detects if air is in the syringe (30) or container having first and second ends. In the case of insulin, the air itself may not be dangerous to the patient, as insulin is not an intravenous injection. However, in said case of insulin, the air may be of significant volume to affect the correct measurement of the volume of medicine in the syringe (30), or container having first and second ends, by displacing said medicine enough to affect measurement of the true amount of medicine. The apparatus (21) can alert medical personnel thru GUI (32) or otherwise if a large enough amount of air is present in the medicine that would affect the volume measurement of said medicine prior to being administered.

Figure 2C:
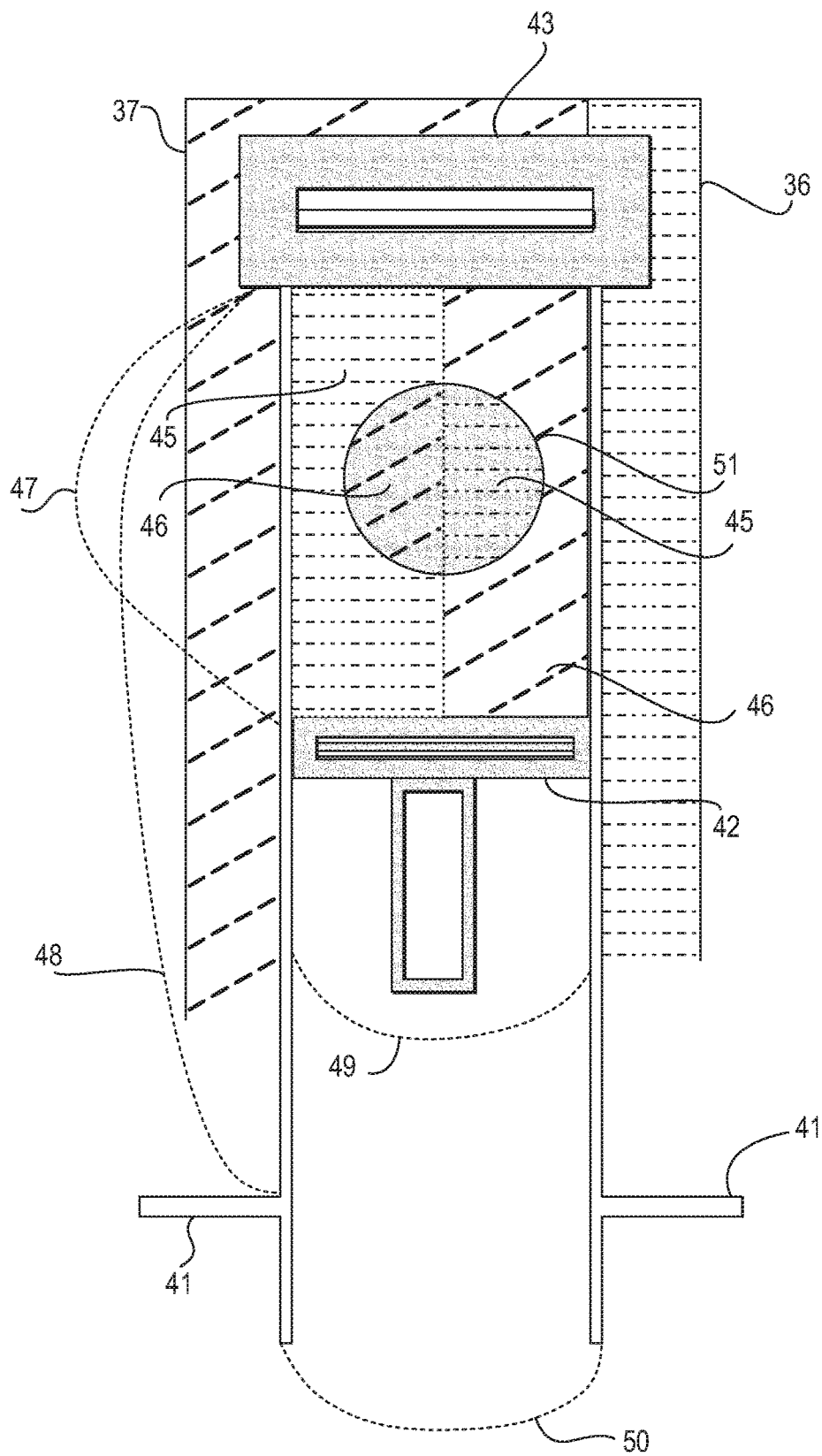
FIG. 2c shows one embodiment of the camera's view of the apparatus of FIG. 1 looking downwards onto the syringe or container having first and second ends full of clear liquid with an air bubble present. The air bubble (51) is straddled between first and second colors of light projecting through the syringe or container having first and second ends.

In the case of intravenous injections, air within the syringe (30), or container having first and second ends, can be dangerous to the patient. The apparatus (21) can alert medical personnel if any potentially harmful amount of air is present in injectable medicine prior to being administered intravenously. FIG. 2c shows one embodiment of the camera's view looking downwards onto the syringe (30) or container having first and second ends full of clear liquid with an air bubble (51) present. The air bubble (51) is straddled between two colors. The colors of light are transposed in the liquid before being viewed by the camera of the apparatus of the invention. Where the air bubble exists, in one embodiment, the colors of light are not transposed before being viewed by the camera of the apparatus of the invention. Thus said air bubble can be discerned, measured, and reported to medical personnel. See discussion below with respect to FIG. 3e and FIG. 3f for the physics of this colored lighting phenomenon. If two or more air bubbles are totally aligned or one air bubble obscures another air bubble which is below the top air bubble, in one embodiment the software can use enough leeway in calculations of area in order to decide on the potential of an unwanted amount of air. If two or more air bubbles are partially aligned, in one embodiment the software can use extrapolation from the visible circumferences in order to measure the area of air and decide on the potential of an unwanted amount of air.

Figure 2D:
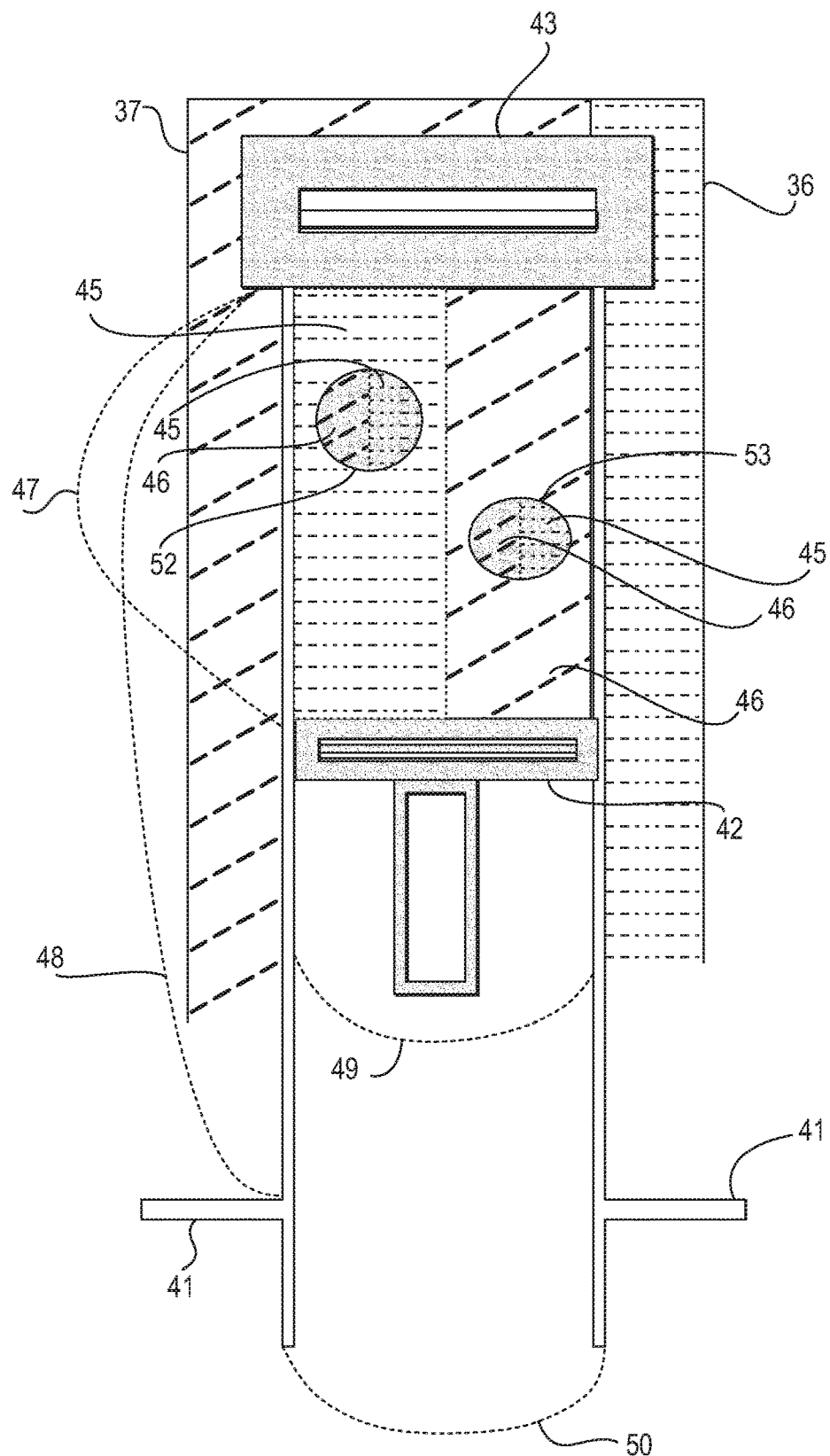
FIG. 2d shows one embodiment of the camera's view of the apparatus of FIG. 1 looking downwards onto a syringe (30), or container having first and second ends, full of clear liquid with two air bubbles (52) and (53) present. Air bubble (52) is surrounded by the color one of two or the first color. Air bubble (53) is surrounded by the color two of two or the second color.

Unlike an air bubble (51) straddled between two colors, air bubbles can also appear enclosed within one color. FIG. 2d shows one embodiment of the camera's (24) view looking downwards onto the syringe (30) or container having first and second ends full of clear liquid with two air bubbles (52,53) present. Air bubble (52) is surrounded by the color one of two or first color. Air bubble (53) is surrounded by the color two of two or second color. The colors of light are transposed in the liquid before being viewed by the camera of the apparatus of the invention, however where the air bubbles exist, the colors of light are not transposed before being viewed by the camera. Thus the bubbles can be discerned, measured, and reported to medical personnel.

Figure 2E:
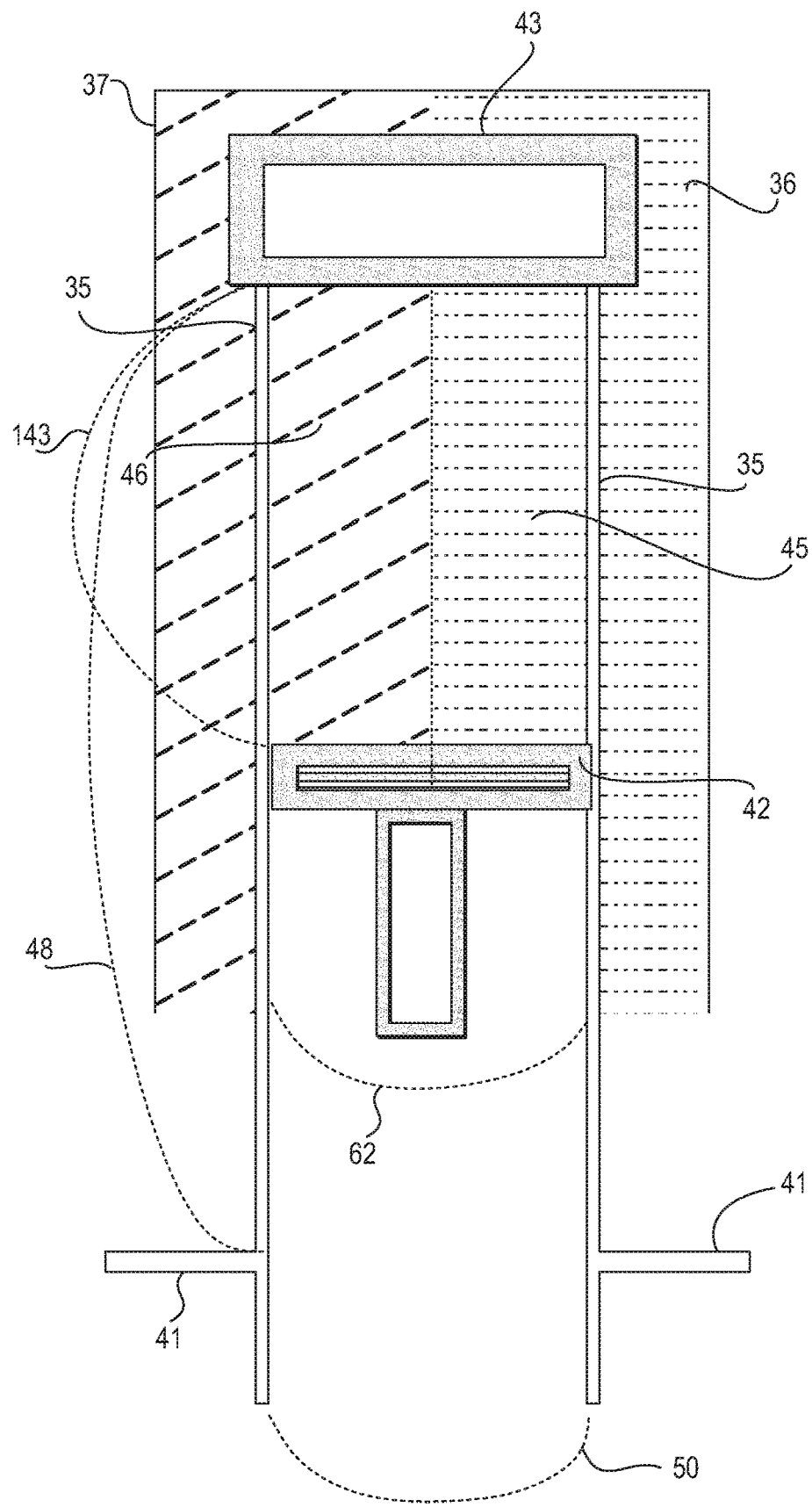
FIG. 2e shows one embodiment of the camera's view of the apparatus of FIG. 1 looking downwards onto the syringe, or container having first and second ends, full of air.

In one embodiment, the apparatus (21) determines if the syringe or container having first and second ends is full or partially full of air. FIG. 2e shows one embodiment of the camera's (24) view looking downwards onto the syringe (30) or container having first and second ends full of air. The colors of light are not transposed as the colors were transposed in liquid before being viewed by the camera of the apparatus of the invention. The length of the air (143) and width of the air (62) are shown, and thus the air can be discerned and measured.

Figure 3A:
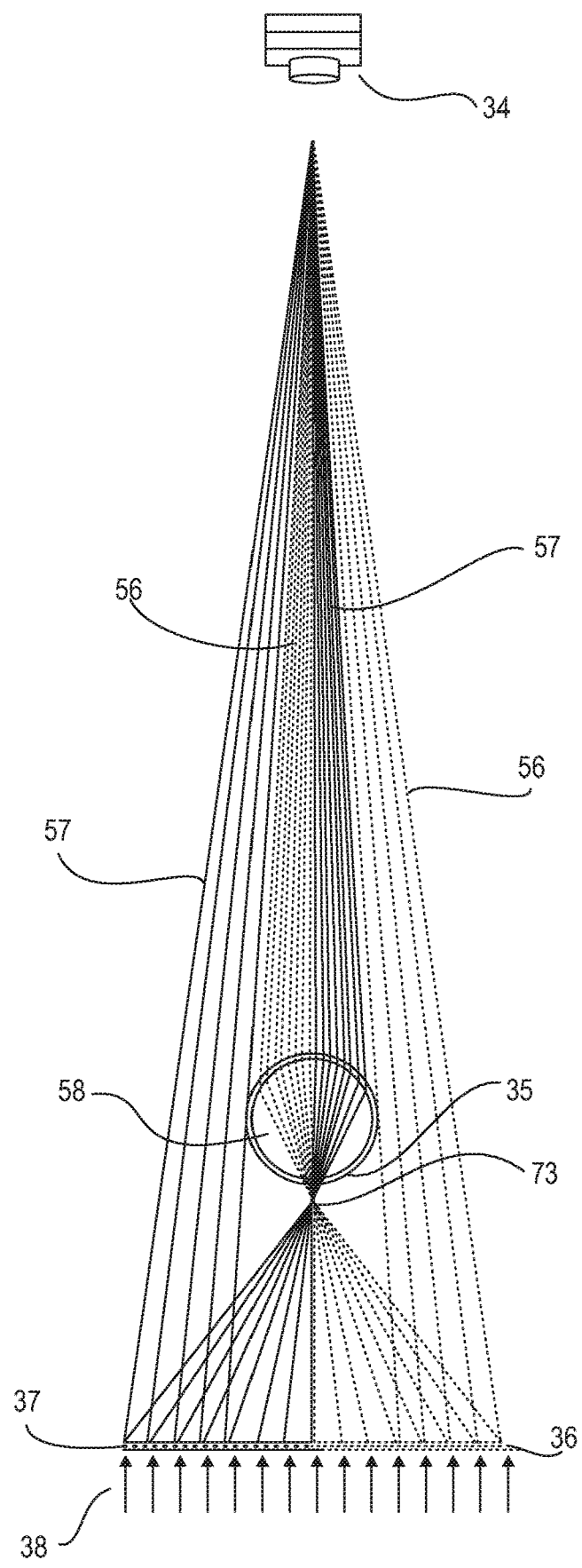
FIG. 3a shows one embodiment of a light ray diagram showing how two colors of light travel upwards through a syringe full of clear liquid and how the first and second colors of the light are transposed before being viewed by a camera of the apparatus of FIG. 1.

The physics of light behavior in air and clear liquid and plastic are used by the apparatus (21) to distinguish the existence of clear liquid within the syringe (30) cylinder, or container having first and second ends, and to distinguish the existence of air within the syringe (30) cylinder or container having first and second ends. FIG. 3a shows one embodiment of a light ray diagram depicting how two colors of light can travel upwards through a cylinder filled with clear liquid (58) and how the light colors are transposed before being viewed by the camera (34) of apparatus (21). The light emanates as white light from the bottom light source (38) and travels upward through one of the two colored transparencies (36,37), or filters, where the white light becomes colored light rays (56,57) by the respective transparency or filter.

The light that travels upward from the bottom light source (38) is omnidirectional and as the light passes through the colored transparencies (36,37) the light remains omnidirectional. The light rays shown in the FIG. 3 drawings are a subset of the infinite amount of light rays being produced. The subset of light rays shown in the FIG. 3 drawings are intended to show the area of light rays which are within the camera's (34) area of view.

Figure 3B:
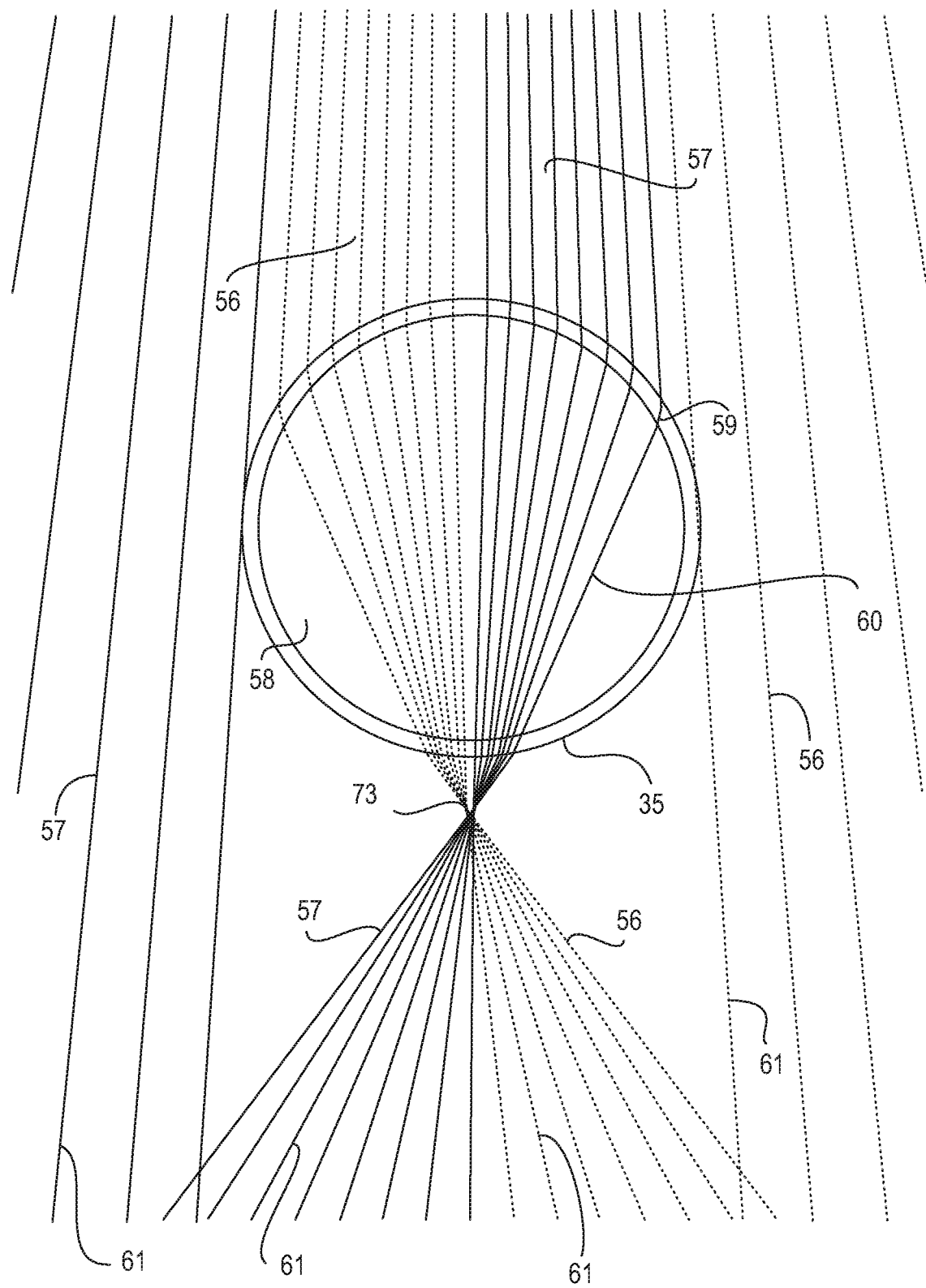

FIG. 3b shows a close-up view of the light refractions of the clear liquid filled cylinder (58) area of the light ray diagram of FIG. 3a. The viewable colored light either passes by the cylinder and is not affected by the cylinder, or the viewable light passes through the cylinder filled with liquid and is refracted (59) according to the refraction index of the plastic wall of the cylinder (35) and the refraction index of the liquid (60) in the clear liquid filled cylinder (58). The light rays (56,57) transpose as they pass through the cylinder and before they reach the camera (34).

FIGS. 3a, 3b, 3c, 3d, 3e, and 3f are all light ray diagrams of an embodiment of the invention. Said light ray diagrams are based on the following:
1. Camera (34) is 3 inches above syringe or container having first and second ends.
2. The syringe (30) cylinder, or container having first and second ends, diameter is ¼"
3. The syringe (30) cylinder, or container having first and second ends, is 1" above transparencies (36,37).
4. Wall thickness of syringe, or container having first and second ends, is 5% of overall diameter.
5. Index of refraction for syringe wall made of PET polypropyline is 1.575
6. Index of refraction for clear liquid insulin is 1.56

Figure 3C:
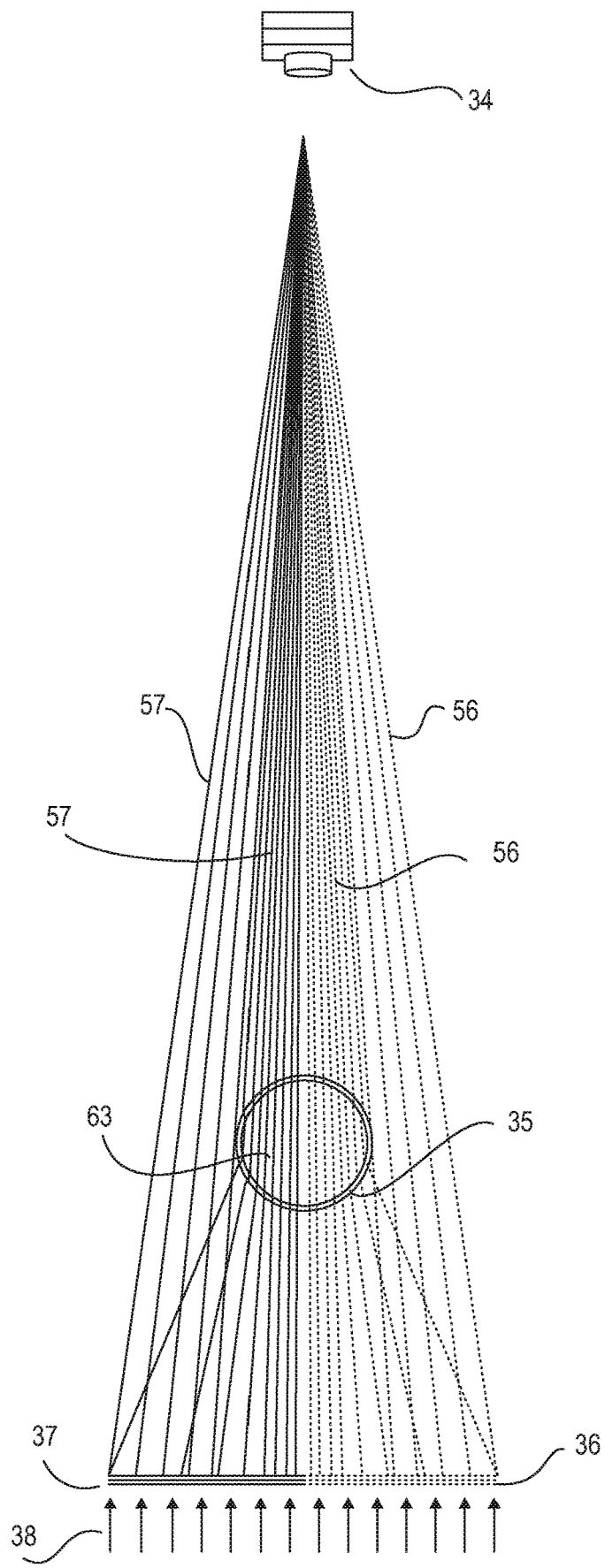
FIG. 3c shows one embodiment of a light ray diagram of how two colors of light travel upwards through a syringe full of air and how the light colors are not transposed before being viewed by a camera of the apparatus of FIG. 1.

FIG. 3c shows one embodiment of a light ray diagram depicting how two colors of light rays (56,57) travel upwards through a cylinder filled with air (63) and how the light's colors are not transposed before being viewed by the camera (34) of the apparatus (21) of the invention of FIG. 1. The light emanates as white light from the bottom light source (38) and travels upward through one of the two colored transparencies (36,37) or filters where the white light becomes colored light rays (56,57) by the respective transparency or filter.

Figure 3D:
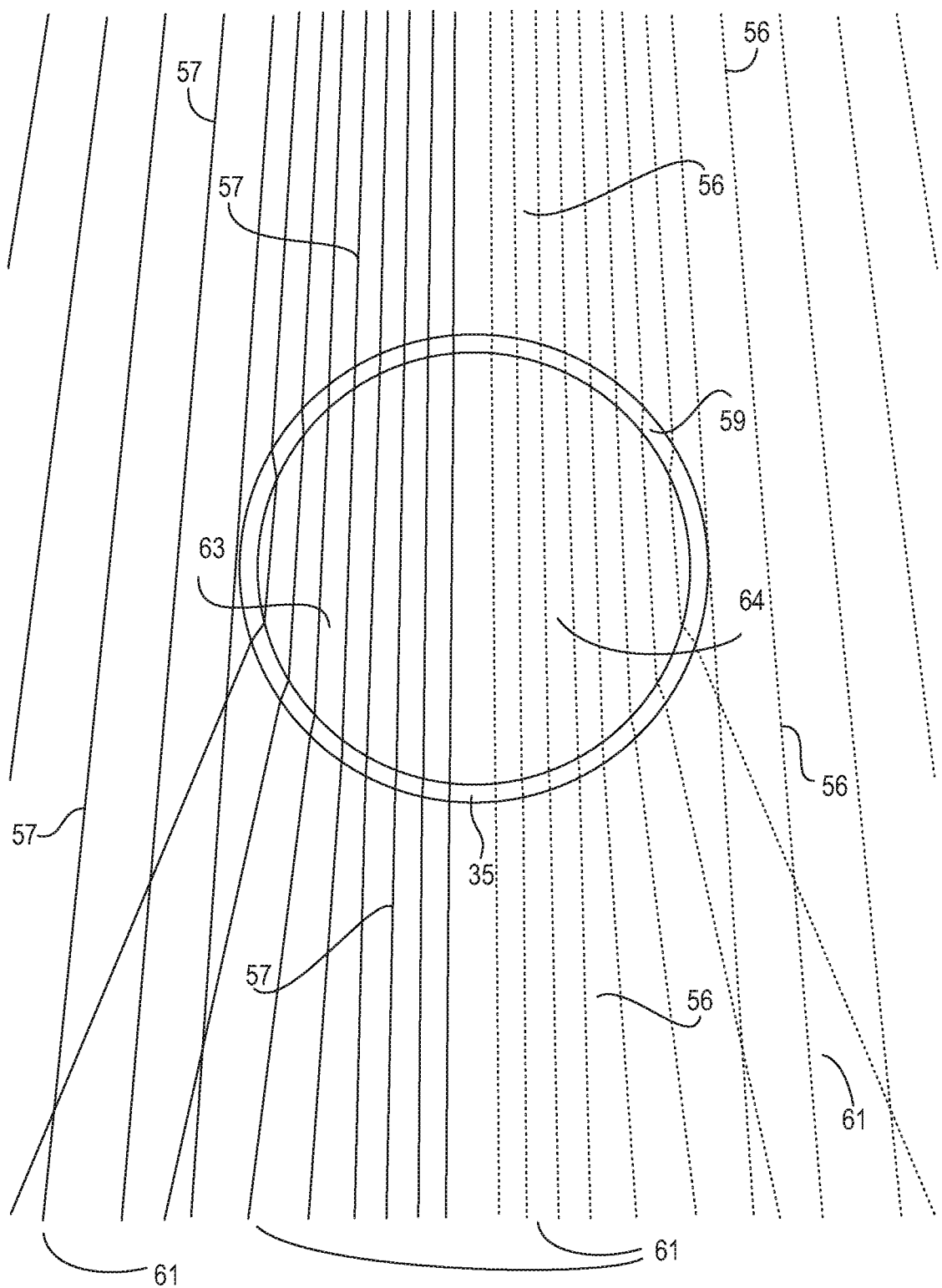
FIG. 3d shows a close-up view of the air filled syringe area of the light ray diagram of FIG. 3c.

FIG. 3d shows a close-up view of the light refractions of the air filled cylinder (63) area of the light ray diagram of FIG. 3c. The viewable colored light either passes by the cylinder and is not affected by the cylinder, or the viewable light passes through the cylinder filled with air and is defracted according to the refraction index of the plastic wall of the cylinder (34) and the refraction index of the air (64) in the air filled cylinder (63). The refraction index of air at standard temperature and pressure is 1.000277. The light rays (56,57) do not transpose as they pass through the air filled cylinder (63) and before they reach the camera (34).

Figure 3E:
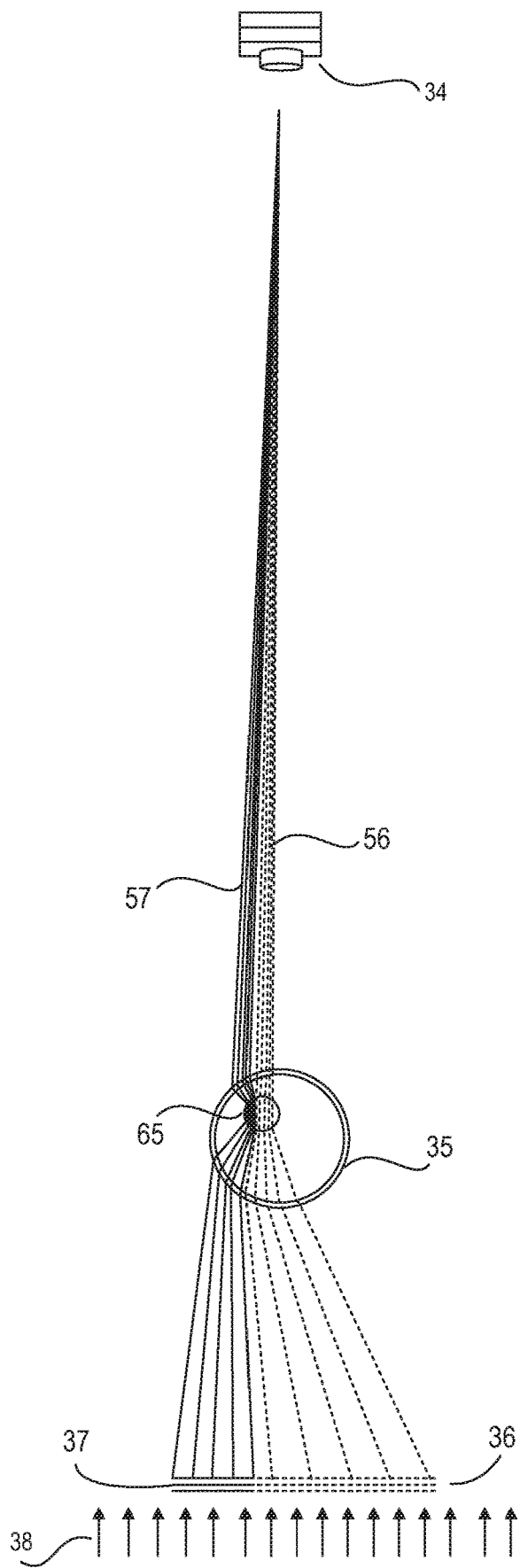
FIG. 3e shows one embodiment of a light ray diagram of how two colors of light travel upwards through a bubble of air in a liquid filled cylinder and how the light colors are not transposed before being viewed by the camera of the apparatus of FIG. 1.

FIG. 3e shows one embodiment of a light ray diagram depicting how two colors of light rays (56,57) travel upwards through a bubble of air (65) in a liquid filled cylinder and shows how the light rays behave if there is a bubble of air in the liquid. The light emanates as white light from the bottom light source (38) and travels upward through one of the two colored transparencies (36,37) or filters where the white light becomes colored light rays (56,57) by the respective transparency or filter.

Figure 3F:
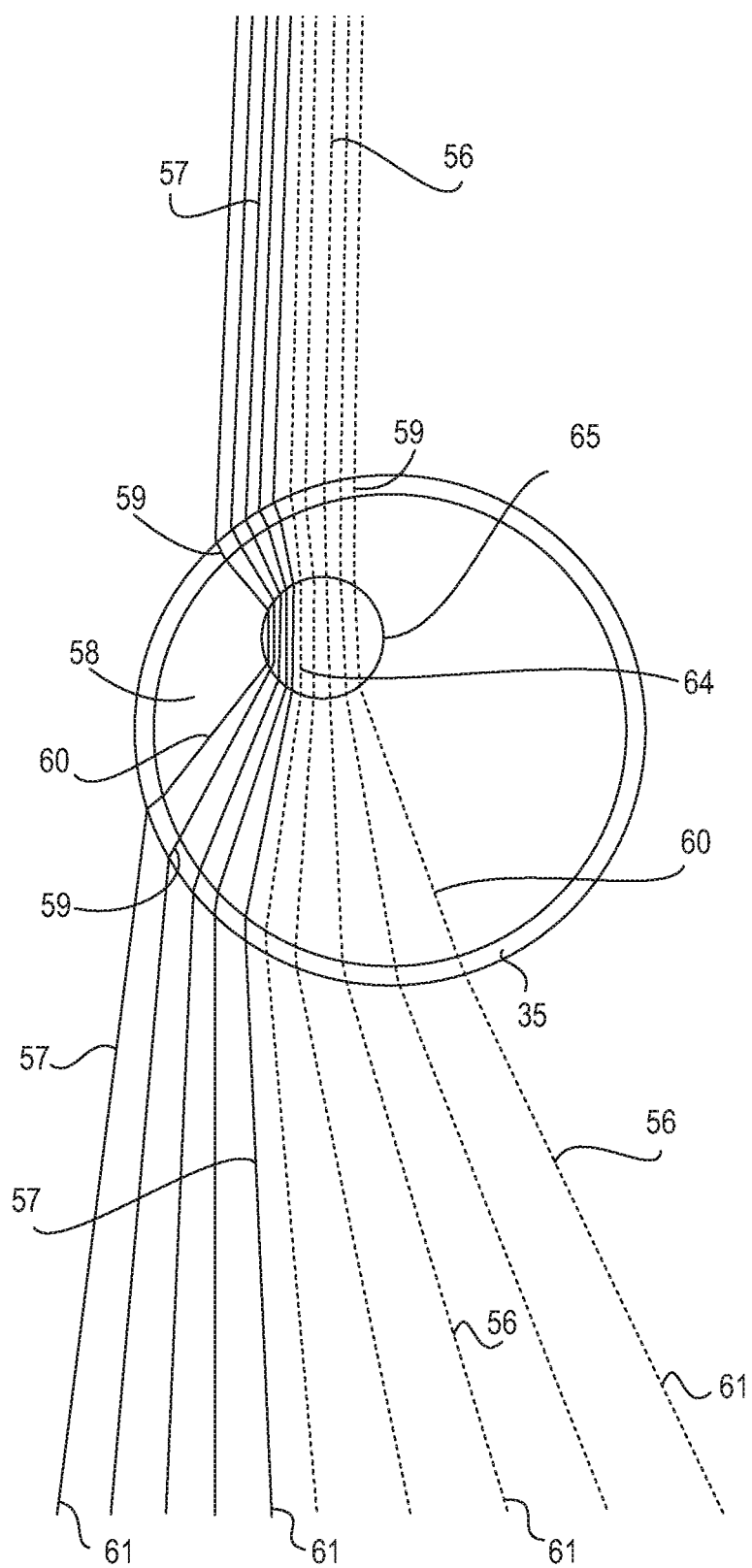
FIG. 3f shows a close-up view of the bubble of air area of the light ray diagram of FIG. 3e.

FIG. 3f is a close up of the bubble area shown in FIG. 3e where light refractions of the air bubble within the liquid in a cylinder occur. FIG. 3f shows that the light rays (61) coming upwards from below the cylinder are refracted first by the cylinder wall (35) and then are refracted in the liquid insulin (60), and then are refracted (64) by the air in the bubble (65).

The light ray then exits the top of the bubble and is refracted again in the liquid and refracted yet again by the upper wall of the cylinder (35). The colors which pass through the bubble of air (65) are not transposed before being viewed by the camera (34) of the apparatus (21) of the invention of FIG. 1. See also FIGS. 2c and 2d for the camera's (34) view of air bubbles within liquid.

The light that travels upward from the bottom light source (38) is omnidirectional and as the light passes through the colored transparencies (36,37), or filters, the light remains omnidirectional. The light rays shown in FIGS. 3e and 3f are a subset of the infinite amount of light rays being produced. The subset of light rays shown in FIGS. 3e and 3f drawings are intended to show the area of the subset of light rays which both pass through the bubble and are within the camera's (34) area of view. Light rays which pass only through liquid and are within the camera's (34) area of view are not shown in FIGS. 3e and 3f.

Figure 4A:
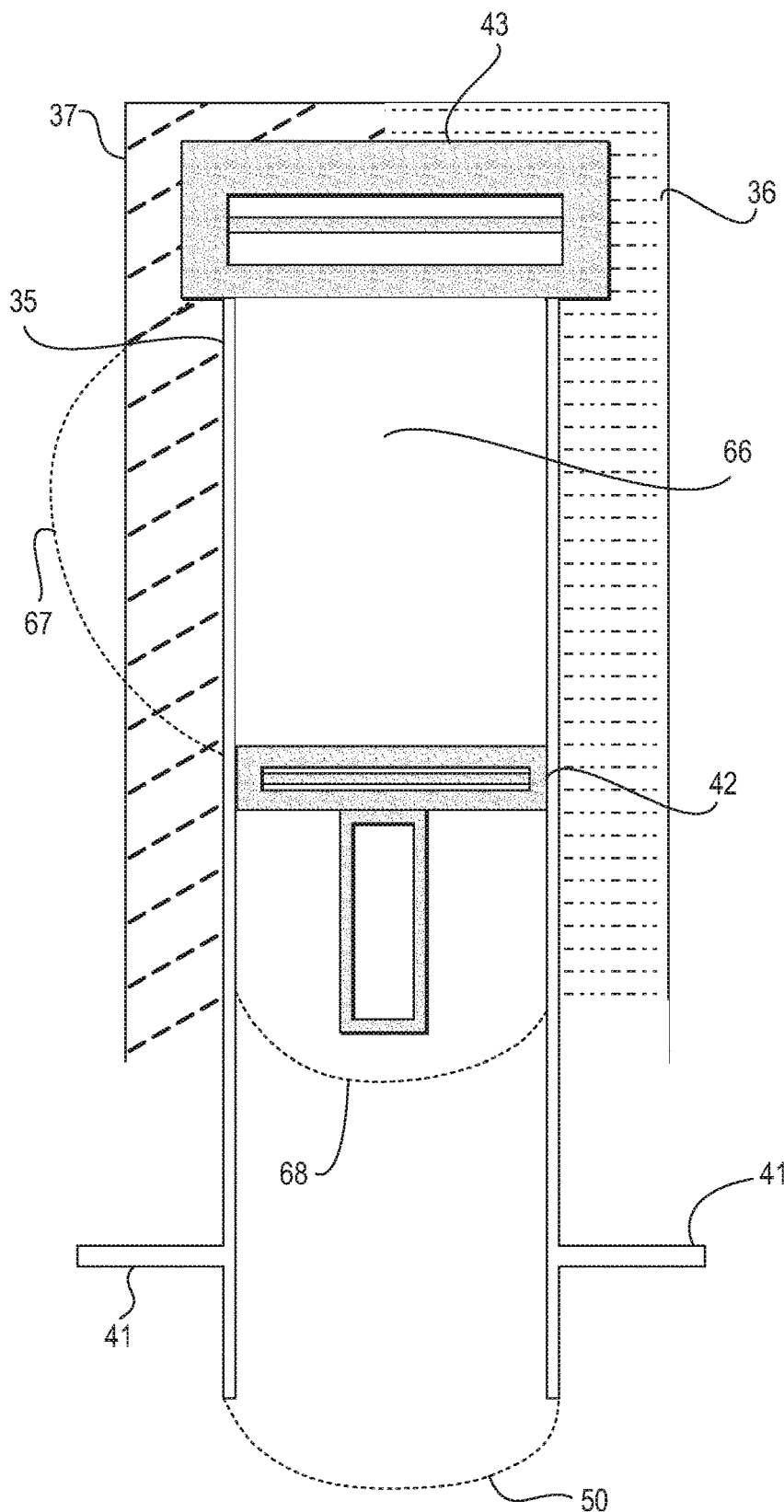
FIG. 4a shows one embodiment of the camera's view of the apparatus of FIG. 1 looking downwards onto the medical dosage device full of Cloudy (White) opaque insulin properly mixed. The colors of light are not able to penetrate the Cloudy (White) opaque insulin properly mixed (66) before being viewed by the camera (34) of the apparatus of FIG. 1a. The length of Cloudy (opaque) insulin in cylinder properly mixed (67) and width of Cloudy (opaque) insulin in cylinder properly mixed (68) are shown, and thus the volume of Cloudy (White) opaque insulin properly mixed (66) can be scanned and measured.

On occasion, the medical personnel may be using cloudy insulin which, when mixed properly may be opaque and not permit the light rays to pass through the insulin so as to be seen by the camera (34). If allowed to settle, cloudy insulin may partially let light thru. FIG. 4a shows one embodiment of what the camera (34) may see if the syringe or container having first and second ends is filled with properly mixed cloudy insulin. Since light rays are not permeating the fluid, the camera (34) sees solid white in the cylinder. In this instance (4a), the computer (24) can easily find the length and width of the opaque medicine by using standard computer vision software (see volume measurement discussion on FIG. 2a above).

Figure 4B:
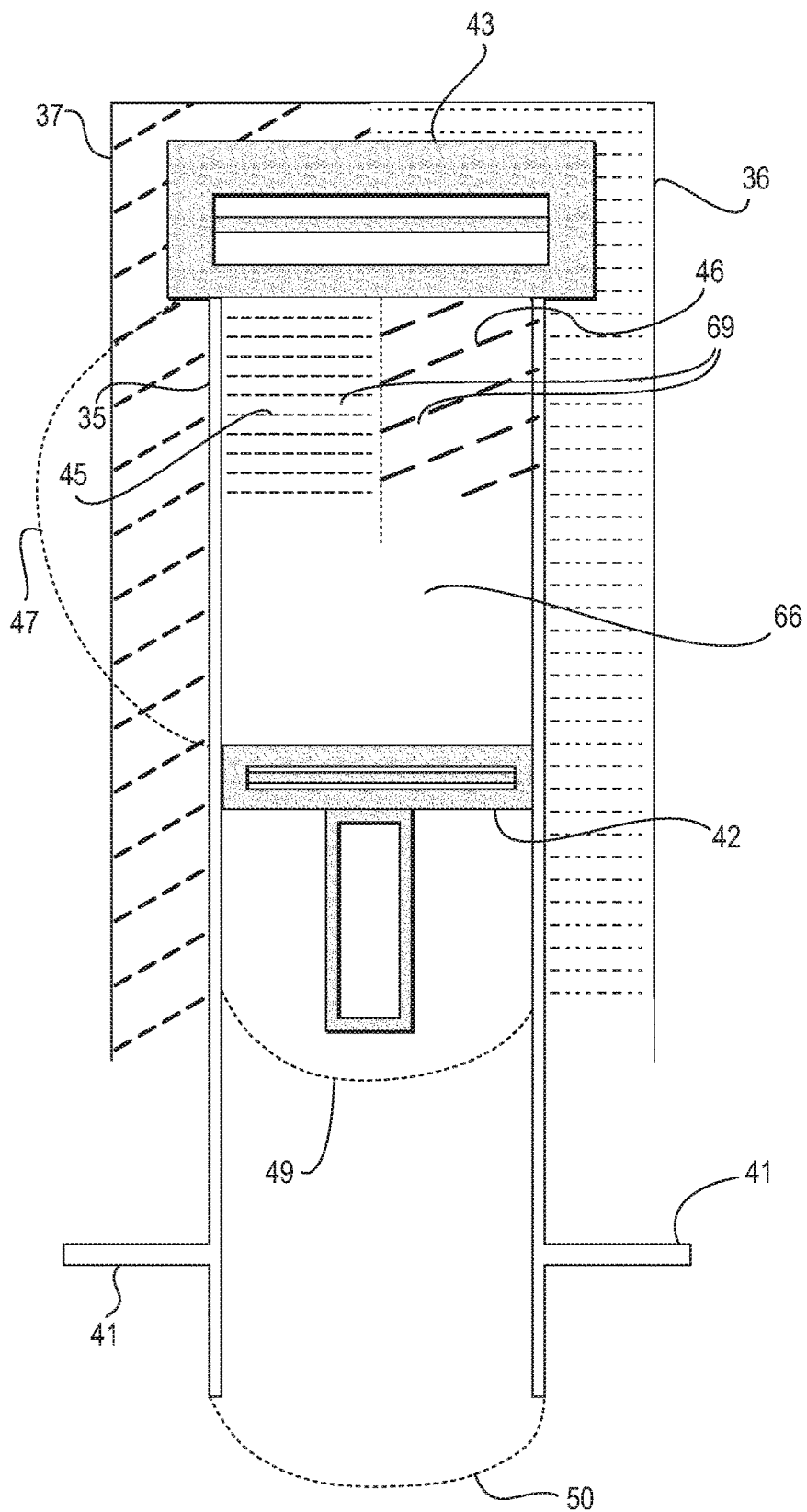
FIG. 4b shows one embodiment of the camera's view of the apparatus of FIG. 1 looking downwards onto the medical dosage device partially filled with Cloudy (White) opaque insulin properly mixed (66) and partially filled with Cloudy insulin whose suspension has settled—becoming clear instead of opaque and letting light thru (69). The length of liquid in cylinder (47) and the width of liquid in cylinder (49) can be measured and thus the volume of liquid in the syringe or container having first and second ends can be evaluated by the apparatus of FIG. 1.

FIG. 4b shows an embodiment where the cloudy insulin has been allowed to partially settle. Where the cloudy insulin permits the partial passage of light, the transposition of light can occur as in a clear liquid (see discussion on transposition of light for FIG. 2a above.) In the situation of FIG. 4b, the apparatus (21) knows how to measure the volume of opaque liquid and clear liquid (see discussion above with respect to FIGS. 4a and 2a).

The apparatus (21) can print a label (23) marked with relevant data and containing a scan code which is to be attached by the medical personnel to syringe (30) or container having first and second ends. Creation of a label (23) can occur upon confirmation of correct dosage and correct medicine and the absence of significant air bubbles in the liquid. The data on label (23) can include, for example, the patient's name and identification, the medical personnel name and identification, the amount of the dose, the current time, the time dosage is due, the unique identification of said embodiment of apparatus (21), the patient database readable barcode with patient, drug, and dose information or any combination of the foregoing.

In one embodiment, the method of apparatus (21), from the point of view of a user, starts as the nurse or medical practitioner logs in (75) on the touchscreen (28). The nurse or medical practitioner enters the name of the applicable patient (76) on the touchscreen (28). The nurse or medical practitioner holds the medicine vial (39) underneath the camera (34) with barcode (40) face up (79). The apparatus (21) decides if the medicine is correct, and if said medicine is correct, the touchscreen (28) is updated and the nurse or medical practitioner is advised to proceed. The nurse or medical practitioner draws the medicine into the syringe and puts the syringe between the guides on the transparent tray of the apparatus (21). The apparatus (21) decides if the amount of medicine in the syringe is correct and safe, and if so, prints a label (23). The apparatus (21) updates a patient database with all pertinent information. The nurse or medical practitioner puts the label on the syringe.

Figure 5:
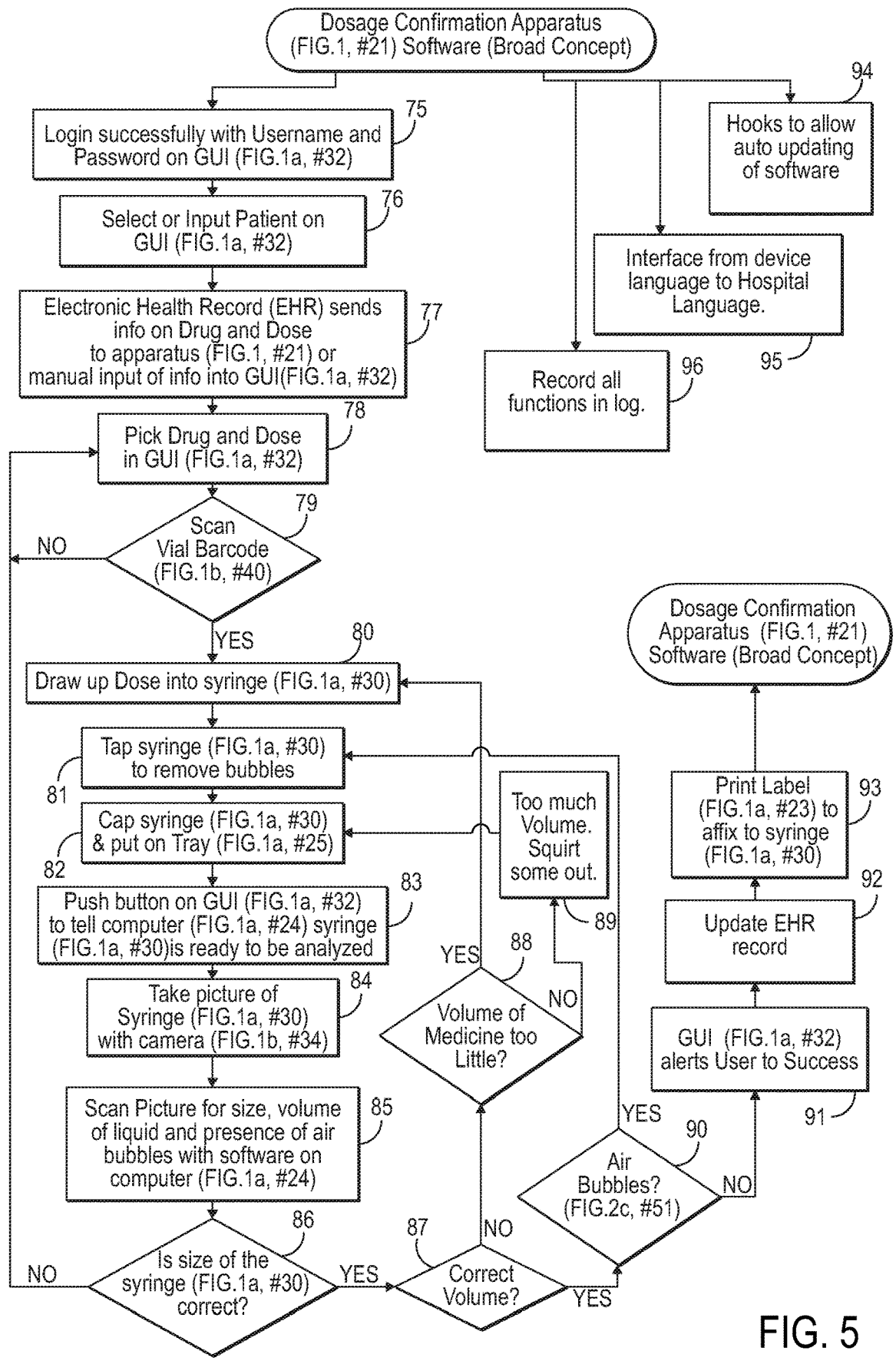
FIG. 5 shows one embodiment of a flowchart delineating the operation of the software of the apparatus FIG. 1.

FIG. 5 shows one embodiment of a flowchart delineating the operation of the software of the apparatus (21). Said embodiment delineates a broad concept of the operation of the software of the apparatus (21). Said flowchart starts with the nurse or medical practitioner accomplishing a successful login (75) using the graphics user interface or GUI (32) on the touchscreen (28). The nurse or medical practitioner enters (76) the current patient using the graphics user interface or GUI (32) on the touchscreen (28). In one embodiment, the apparatus (21) is in communication with a patient database or Electronic Health Record (EHR) of the patient and the software can receive (77) all pertinent data on the patient and can display pertinent data using GUI (32). All pertinent data of the patient, for example the patient's EHR, can be stored in the memory of the apparatus (21), stored in memory remote of the apparatus (21), for example offsite of the apparatus (21), or stored in any combination of the foregoing. In one embodiment, the nurse or medical practitioner manually enters (77) the pertinent data of said current patient using GUI (32). The nurse or medical practitioner picks (78) the type of drug or medicine using GUI (32). The nurse or medical practitioner enters (78) the dosage of said drug or said medicine using GUI (32). The nurse or medical practitioner holds a vial of medicine (39) below the camera (34), the camera takes a picture of the label (79) of said vial (39) of medicine, and the software analyzes (79) the image of the barcode on the label (40) of said vial (39) of medicine, and the software decides (79) if said vial of medicine is the correct medicine. If the vial (39) of medicine is not correct, the GUI (32) asks the nurse or medical practitioner to redo the process of picking the medicine (78). If the vial (39) of medicine is correct, the GUI (32) asks the nurse or medical practitioner to draw (80) the medicine into a syringe, and the GUI (32) asks the nurse or medical practitioner to tap the syringe to eliminate air bubbles (81), and the GUI (32) asks the nurse or medical practitioner to place (82) the cap (43) or first end on to the syringe (30) or container. GUI (32) asks the nurse or medical practitioner to place (82) the syringe (30), or container having first and second ends, on top of the transparent tray (25). The nurse or medical practitioner pushes a button on GUI (32) to alert the software that the syringe (30) is ready for analysis (83). The camera (34) takes a picture (84) of the syringe (30). The software scans (85) said picture and the software analyzes the data to determine (85) if the syringe is the correct size, to determine (85) the volume of liquid, and to determine (85) the presence of air or air bubbles present in the syringe (30). If the size of the syringe (30) is not correct (80), the software goes back to step (78) and the GUI (32) asks the nurse or medical practitioner to pick the medicine or drug and dose (78). If the size of the syringe (30) is correct (80), the software decides if the volume of medicine or the volume of drug is correct (86). and the GUI (32) asks the nurse or medical practitioner to pick the medicine or drug and dose (78). If the volume of medicine or the volume of drug is not correct, the software decides if there is too much volume (89) or too little volume (88). If there is too little volume (88) then GUI (32) takes the nurse or medical practitioner back to draw up more medicine (80) into the syringe (30). If there is too much volume (88) then GUI (32) asks the nurse or medical practitioner to squirt out an amount of the medicine which can allow for proper volume to be achieved, then GUI (32) asks the nurse or medical practitioner to recap the syringe (82). If the volume is correct (87) then the software analyzes the picture to determine if there is air or air bubbles (90) in the syringe (30). If there is a harmful amount of air detected by the software, the GUI (32) asks the nurse or medical practitioner to tap the syringe to eliminate air bubbles (81). If there is not a harmful amount of air detected by the software, the GUI (32) alerts the nurse or medical practitioner of success (91). The software updates the electronic health record EHR if an EHR is available (92). The software tells the printer (22) to print (93) a label (23) for the nurse or medical practitioner to affix to the syringe (30) or container having first and second ends.

Figure 6B:
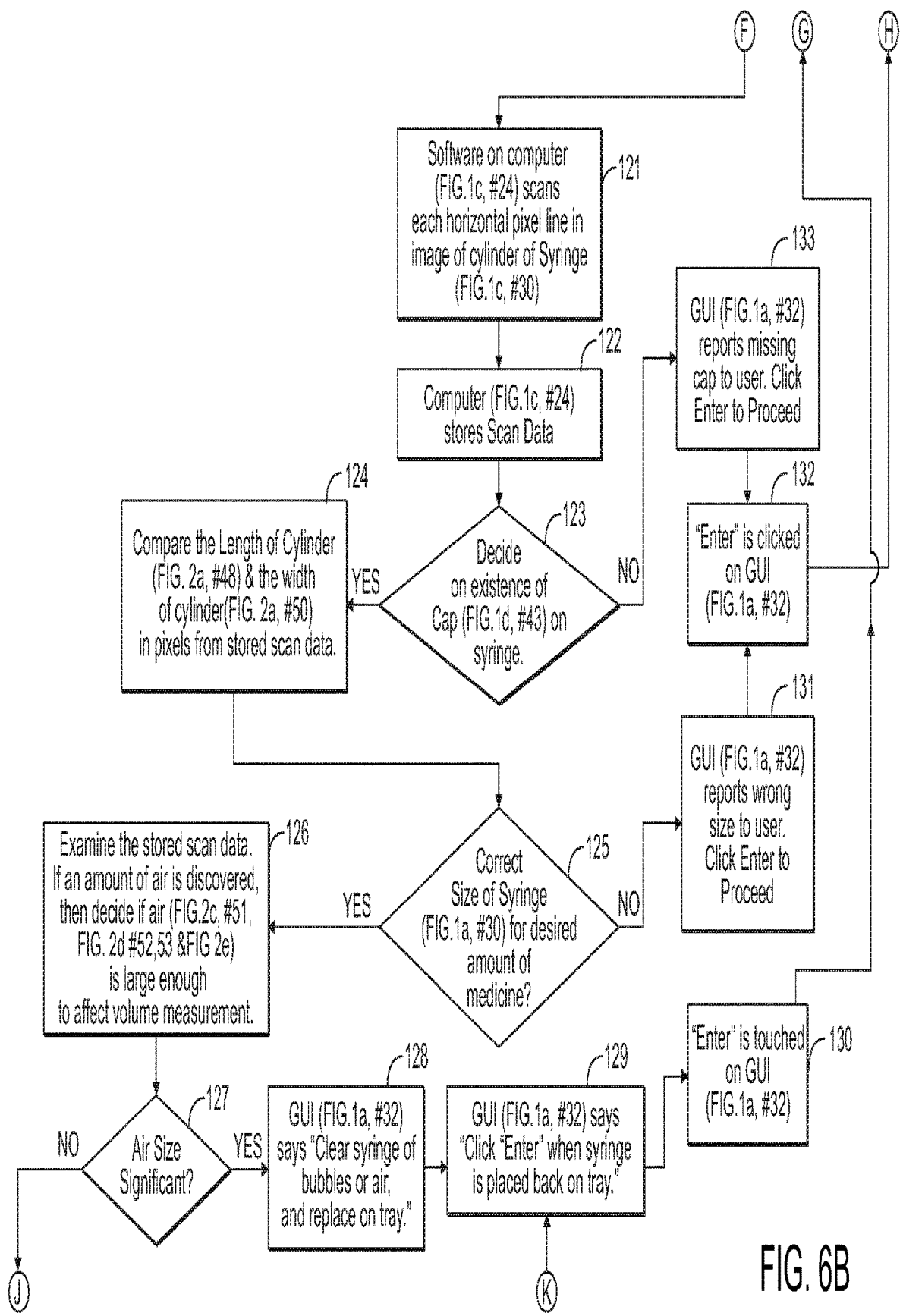
Figure 6C:
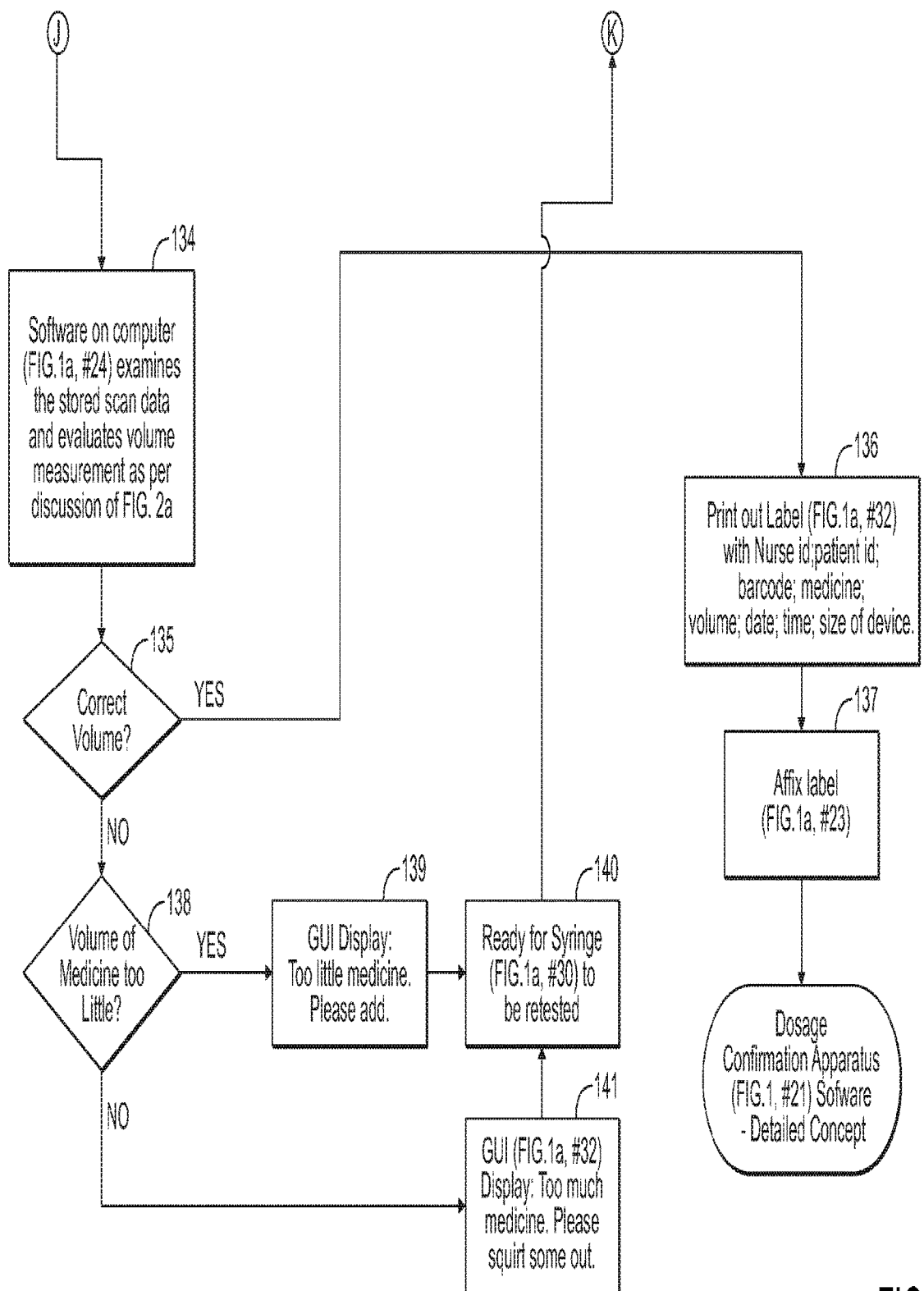

FIG. 6a-6c show one embodiment of a flowchart delineating the operation of the software of the apparatus (21). Said embodiment delineates a more detailed concept of the operation of the software of the apparatus (21) than FIG. 5. Said flowchart starts (FIG. 6a) with the nurse or medical practitioner tapping the graphics user interface or GUI (32) on the touchscreen (28) to wake up the sleeping computer (24) if needed (97). The GUI (32) on the touchscreen (28) displays the login screen (98). The nurse or medical practitioner enters username and password, then presses the "Enter" button (99). Alternatively, the nurse or medical practitioner scans their Identification Badge, enters password, then presses the "Enter" button (99). The software decides as to whether the login is authentic (100). If the login is not authentic, an alert states that "Login Failed", and the nurse or medical practitioner can revisit step (99) and try to login again. If the login is authentic, the nurse or medical practitioner selects (102) the current patient using the graphics user interface or GUI (32) on the touchscreen (28). The software determines if the patient identifier is recognized as valid (103). If the software determines that the patient identifier is not valid, the graphics user interface or GUI (32) displays an alert to try again (104) and step (102) is repeated. If the software determines that the patient identifier is valid, then the software extracts pertinent patient information from the patient database (105) or, if said patient information is not available, asks the nurse or medical practitioner to enter the information (105) in the graphics user interface or GUI (32) on the touchscreen (28). Said information may include, but is not limited to, type of medicine; dosage of medicine required; and blood glucose level. Said information is displayed (106) on the graphics user interface or GUI (32) on the touchscreen (28). The graphics user interface or GUI (32) tells the nurse or medical practitioner to position a vial of medicine below the camera (34) on the transparent tray (25) between guides (27) with the barcode on the label facing upwards (107). The nurse or medical practitioner presses the "Enter" button (108) in the graphics user interface or GUI (32) on the touchscreen (28) when the vial is in position. Software on computer (24) instructs (109) camera (34) to read barcode (40). Software compares information (109) on barcode (40) to information the software already has acquired of the patient, and software analyzes if the medicine is the correct type of medicine for the patient (110). If the vial of medicine is not correct, the GUI (32) alerts the nurse or medical practitioner with a message "Wrong medicine or misread" (112). GUI (32) asks the nurse or medical practitioner to redo the process of positioning correct medicine (107). If the vial of medicine is correct, the GUI (32) alerts the nurse or medical practitioner (111) "Medicine Correct. Please place filled syringe on tray between the guides, being sure that the wings or flanges of the syringe are on the tray." The GUI (32) alerts the nurse or medical practitioner (119) to press "Enter" button when ready. When the nurse or medical practitioner presses the "Enter" button, the software instructs the camera (34) to take a picture (120).

FIG. 6b continues the flow of one embodiment of a flowchart delineating the operation of the software of the apparatus (21). Software scans each horizontal pixel line (121) in image of syringe (30) or container having first and second ends. Software stores scanned data (122) for analysis. Software decides (123) on the existence of a cap (43) or first end in place on the top of the syringe (30) or container. If the cap or first end is not in place, the GUI (32) reports to the nurse or medical practitioner that the cap or first end is missing and to touch "Enter" to proceed (133). The software sends the user back to step #111. If the cap or first end is in place, the software assesses the length in pixels of the cylinder (48) of the syringe (30), or container having first and second ends, and the width of the cylinder (48) of the syringe (30), comparing (124) the length and width of the cylinder (48) of the syringe (30), or container having first and second ends, to a library of known lengths and known widths of known sizes of syringes (30) or containers having first and second ends. The software determines (125) if the calculated size of the syringe, or container having first and second ends, is the proper size for the present dosage amount. If the calculated size of the syringe, or container having first and second ends, is not the proper size, GUI (32) reports the wrong size to the user. GUI (32) alerts the nurse or medical practitioner (119) to press "Enter" button when ready. The software sends the user back to step #111. If the calculated size of the syringe, or container having first and second ends, is the proper size, the software can analyze the stored scan data and determine (126) if there is an amount of air discovered which is significant to the current application of the dose. If there is said amount of air, then GUI (32) says (128) "Clear syringe of bubbles or air, and replace on tray." GUI (32) says (129) "Click Enter when syringe is placed back on tray." When "Enter" is touched (130) on GUI (32), the software restarts at #120 by taking another picture. If there is not a significant amount of air found in step #127, FIG. 6c shows that the software examines the stored scan data and evaluates (134) volume measurement of medicine in the syringe (30). If the volume of medicine (135) is not correct, then the software must decide if the volume of medicine is too little or too much. If the volume is too little (138) GUI (32) displays (139) "Too little medicine. Please add". If the volume is too much GUI (32) displays (141) "Too much medicine. Please squirt some out." The software is alerted when the syringe, or container having first and second ends, is ready to be retested (140). The software then goes to step #129 and proceeds again from step #129. If the volume is correct the software prints out label (23) with pertinent information (136) such as nurse id or medical practitioner id, patient id, medicine, volume, date, time, size of device. The nurse or medical practitioner affixes (137) the label to the syringe or container having first and second ends.

Several advantages may occur from the invention, for example with the use of an embodiment of apparatus (21). The amount of adverse medical events involving incorrect dosage can decrease and therefore can save lives and can ease suffering. Time can be saved by the apparatus' (21) processing taking less time than the time needed to locate a second nurse and having said second nurse check the accuracy of the first nurse's work. Accurate patient specific barcode for each dose can be provided. Links between diet and dose and blood glucose level may be able to be analyzed due to the apparatus recording the data of each filling of syringes (30) or containers having first and second ends. Economic savings can occur due to the number of insulin pens decreasing. More effective treatment of said patient after release from the hospital can be achieved by the apparatus' (21) recording of past dosages of insulin and analyzing said dosages' relationship to blood glucose levels. The open design can allow for easier cleaning, and therefore thorough sanitation. The artificial intelligence invented for the apparatus (21) that allows a machine to easily and inexpensively tell the difference between air and clear liquid in a cylinder is a large advance in robotic vision. Other advantages of one or more aspects can be apparent from a consideration of the drawings and the drawings' descriptions.

In one embodiment, an apparatus for use with computer memory having stored characteristics of a plurality of known containers to determine the volume of a liquid in one of the plurality of known containers having first and second ends for defining the volume of liquid is provided and includes a digital camera adapted for viewing the container, a processor electrically coupled to the camera and configured to optically detect certain characteristics of the container viewed by the camera and to access the computer memory having stored characteristics of the plurality of known containers, the processor being configured to compare the detected certain characteristics with the stored characteristics to identify the container from the plurality of known containers, the processor being configured to calculate the volume of the container as a function of the distance between the first and second ends of the container as viewed by the camera.

The apparatus can include an input interface for receiving the identity of the liquid and a printer, the processor being configured to cause the printer to print a label which includes the identity of the liquid. The processor can be configured to determine whether the container is filled entirely with the liquid. The apparatus can be configured to provide a first output signal if the container is entirely filled with the liquid and a second output signal if the container is not entirely filled with the liquid. The apparatus can include a light assembly for projecting first and second colors of light through the container, wherein the processor is configured to determine whether the container is filled entirely with the liquid by analyzing a pattern of the first and second colors emitted from the container and viewed by the camera. The processor can be configured to determine whether the container is filled entirely with air by analyzing a pattern of the first and second colors emitted from the container and viewed by the camera. The processor can be configured to determine whether the container contains bubbles of air by analyzing a pattern of the first and second colors emitted from the container and viewed by the camera. The apparatus can include a structure having a support for receiving the container, wherein the light assembly is carried by the structure and the camera is carried by the structure opposite the light assembly relative to the container. The light assembly can include a light source and a first filter of the first color and a second filter of the second color disposed alongside the first filter so that a first portion of the light from the light source travels through the first filter and a second portion of the light from the light source travels through the second filter. The pattern of the first and second colors can include the first color disposed alongside the second color. The container can be a syringe having a barrel and a plunger, the barrel having a first end provided with a fluid exit port and a second provided with an opening and the plunger having an end for extending through the opening in the barrel for slidable disposition in the barrel, the first end of the container being the first end of the barrel and the second end of the container being the end of the plunger. The apparatus can include a printer, the processor being configured to cause the printer to print a label which includes the dose of the liquid.

In one embodiment, an apparatus for use in determining the presence of any air pockets in a volume of a liquid in a container is provided and includes a digital camera adapted for viewing the liquid within the container and providing at least one image of the liquid within the container and a processor electrically coupled to the camera for receiving the at least one image from the camera and configured to determine whether the liquid contains any air pockets based on the at least one image.

The apparatus can be configured to provide a first output signal if the liquid does not contain any air pockets and a second output signal if the liquid does contain any air pockets. The apparatus can include an input interface for receiving the identity of the liquid and a printer, the processor being configured to cause the printer to print a label which includes the identity of the liquid. The processor can be configured to print the label only if the liquid does not contain any air pockets. The apparatus can include a light assembly for projecting first and second colors of light through the container, wherein the processor is configured to determine whether the liquid contains any air pockets by analyzing a pattern of the first and second colors emitted from the container and viewed by the camera. The apparatus can include a structure having a support for receiving the container, wherein the light assembly is carried by the structure and the camera is carried by the structure opposite the light assembly relative to the container. The light assembly can include a light source and a first filter of the first color and a second filter of the second color disposed alongside the first filter so that a first portion of the light from the light source travels through the first filter and a second portion of the light from the light source travels through the second filter. The pattern of the first and second colors can include the first color disposed alongside the second color. The apparatus can include a printer, the processor being configured to cause the printer to print a label which includes the dose of the liquid.

In one embodiment, a method for use by an apparatus having a camera and a processor electrically coupled to the camera to confirm the dosage of a medicament in a container is provided and includes accessing the proper volume of the dosage from computer memory, viewing the container with the camera to obtain at least one image of the container, delivering the at least one image of the container to the processor, calculating the volume of the liquid in the container utilizing the at least one image and comparing the calculated volume to the proper volume.

The computer memory can be remote from the apparatus. The proper volume can be included in a patient's electronic health record stored in the computer memory remote from the apparatus. The computer memory can be included in the apparatus and electrically coupled to the processor.

What is claimed is:

1. An apparatus for use with a container to analyze a volume of a liquid in the container, comprising:
 a light assembly configured to project first and second different colors of light simultaneously through the entire container to determine whether the container is filled entirely with the liquid, the first and second colors emitted from the container in a first pattern when the container is filled entirely with the liquid and in a second pattern when the container is not filled entirely with the liquid,
 a digital camera adapted for viewing the container,
 a processor electrically coupled to the camera and configured to analyze the pattern of the first and second colors emitted from the container and viewed by the camera so as to determine whether the container is filled entirely only with the liquid.

2. The apparatus of claim 1, further comprising an input interface for receiving the identity of the liquid and a printer, the processor being configured to cause the printer to print a label which includes the identity of the liquid.

3. The apparatus of claim 1, wherein the processor is configured to analyze the pattern of the first and second colors emitted from the container and viewed by the camera so as to determine whether the container is filled partially with air.

4. The apparatus of claim 1, wherein the processor is configured to provide a first output signal if the container is entirely filled with the liquid and a second output signal if the container is not entirely filled with the liquid.

5. The apparatus of claim 1, wherein the container has first and second ends for defining the volume of liquid and wherein the processor is configured to calculate the length of the liquid in the container as a function of the distance between the first and second ends of the container as viewed by the camera.

6. The apparatus of claim 5, wherein the container is a syringe having a barrel and a plunger, the barrel having a first end provided with a fluid exit port and a second end provided with an opening and the plunger having an end for extending through the opening in the barrel for slidable disposition in the barrel, the first end of the container being the first end of the barrel and the second end of the container being the end of the plunger.

7. The apparatus of claim 1, wherein the processor is configured to analyze the pattern of the first and second colors emitted from the container and viewed by the camera for any light refracted by the container in a first manner surrounded by light refracted by the container in a second manner so as to determine whether the container contains any bubbles of air.

8. The apparatus of claim 1, further comprising a structure having a support for receiving the container, wherein the light assembly is carried by the structure and the camera is carried by the structure opposite the light assembly relative to the container.

9. The apparatus of claim 1, wherein the light assembly includes a light source and a first filter of the first color and a second filter of the second color disposed alongside the first filter so that a first portion of the light from the light source travels through the first filter and a second portion of the light from the light source travels through the second filter.

10. The apparatus of claim 9, wherein each of the first pattern and the second pattern includes the first color disposed alongside the second color.

11. The apparatus of claim 1, further comprising a printer coupled to the processor, the processor being configured to cause the printer to print a label which includes the dose of the liquid.

12. The apparatus of claim 1, wherein the container is a closed container.

13. An apparatus for use with a volume of a liquid in a container, comprising:
 a light assembly configured to project first and second different colors of light through the container to detect any air pockets in the volume of liquid in the container,
 a digital camera adapted for viewing the liquid within the container and providing at least one image of the liquid within the container and the first and second colors emitted from the container, and
 a processor electrically coupled to the camera for receiving the at least one image from the camera and configured to analyze the image for any first and second colors of light refracted by the liquid within the container in a first manner surrounded by first and second colors of light refracted by the liquid within the container in a second manner so as to determine whether the liquid contains any air pockets.

14. The apparatus of claim 13, wherein the processor is configured to provide a first output signal if the liquid does not contain any air pockets and a second output signal if the liquid does contain any air pockets.

15. The apparatus of claim 13, further comprising an input interface for receiving the identity of the liquid and a printer, the processor being configured to cause the printer to print a label which includes the identity of the liquid.

16. The apparatus of claim 15, wherein the processor is configured to print the label only if the liquid does not contain any air pockets.

17. The apparatus of claim 13, further comprising a structure having a support for receiving the container, wherein the light assembly is carried by the structure and the camera is carried by the structure opposite the light assembly relative to the container.

18. The apparatus of claim 13, wherein the light assembly includes a light source and a first filter of the first color and a second filter of the second color disposed alongside the first filter so that a first portion of the light from the light source travels through the first filter and a second portion of the light from the light source travels through the second filter.

19. The apparatus of claim 13, wherein the first and second colors emitted from the container includes a pattern of the first color disposed alongside the second color.

20. The apparatus of claim 13, further comprising a printer coupled to the processor, the processor being configured to cause the printer to print a label which includes the dose of the liquid.

21. A method for use by an apparatus having a camera and a processor electrically coupled to the camera to confirm a liquid dosage of a medicament in a container, comprising:
 accessing a proper volume of the liquid dosage from computer memory,
 viewing the container with the camera to obtain at least one image of light that has passed through the liquid and the entire container,
 delivering the at least one image to the processor,
 calculating a volume of the liquid in the container utilizing the at least one image, and
 comparing the calculated volume of the liquid in the container to the proper volume of the liquid dosage.

22. The method of claim 21, wherein the viewing step includes viewing the container with the camera to obtain at least one image of a pattern of first and second colors emitted from the container.

23. The method of claim 21, wherein the proper volume is included in a patient's electronic health record stored in the computer memory remote from the apparatus.

24. The method of claim 21, wherein the computer memory is included in the apparatus and electrically coupled to the processor.

* * * * *